(12) United States Patent
Kawamura et al.

(10) Patent No.: US 6,685,471 B1
(45) Date of Patent: *Feb. 3, 2004

(54) TOOTH BRUSHING DEVICE WITH VIDEO SCOPE

(75) Inventors: Taturou Kawamura, Kyotanabe (JP); Hiroshi Nakayama, Hirakata (JP); Kiyoko Ooshima, Shijonawate (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 426 days.

This patent is subject to a terminal disclaimer.

(21) Appl. No.: 09/713,977

(22) Filed: Nov. 16, 2000

(30) Foreign Application Priority Data

Nov. 19, 1999 (JP) ............................. 11-330524
Dec. 16, 1999 (JP) ............................. 11-358120

(51) Int. Cl.⁷ ..................... A61C 17/22; A61C 19/00; A46B 9/04
(52) U.S. Cl. ..................... 433/29; 15/22.1; 15/105; 15/167.1
(58) Field of Search ............ 15/22.1, 105, 167.1; 433/29

(56) References Cited

U.S. PATENT DOCUMENTS 5,429,502 A * 7/1995 Cooper et al. .............. 433/29
5,743,731 A * 4/1998 Lares et al. ................. 433/29
5,836,762 A * 11/1998 Peithman .................... 433/29
5,908,294 A * 6/1999 Schick et al. ............... 433/29
6,181,369 B1 * 1/2001 Ooshima et al. ......... 433/29 X
6,468,076 B2 * 10/2002 Kawamura ................. 433/29

FOREIGN PATENT DOCUMENTS

| EP | 280 823 | 9/1988 |
|---|---|---|
| RU | 2041689 | 8/1995 |
| WO | 98/15236 | 4/1998 |

* cited by examiner

*Primary Examiner*—Mark Spisich
(74) *Attorney, Agent, or Firm*—RatnerPrestia

(57) ABSTRACT

A tooth brushing device with a video scope including a video scope having a prism mirror 10 and an objective lens 9 that form light from an object into an image, a CCD unit 8 that converts the light formed into the image, into an electric signal, and a handle section 7 held by an operator, a tooth brush having a brush section having a cavity portion 4 formed therein and a handle section held by the operator, and a display section for displaying an image picked up by the video scope, in which the handle section of the toothbrush is integrated with the handle section 7 and the prism mirror 10 is arranged where a clear image of a tooth to be brushed by the operator is picked up by the video scope. When images are picked up through the cavity portion 4 formed in the brush section and a toothbrush section and an image pickup section are independently installed in the handle section 7, images can be picked up even during a tooth brushing operation.

39 Claims, 19 Drawing Sheets

TOOTH BRUSHING DEVICE WITH VIDEO SCOPE

BACKGROUND OF THE INVENTION

1. Field of the Invention

The present invention relates to a video scope for picking up an image of an inside of a mouth, the video scope having a built-in image pickup element, for example, a CCD, and to a toothbrush.

2. Description of the Related Art

A video scope using a CCD capable of picking up an image of a local site while illuminating it has often been used by dentists or oral surgeons to diagnose the inside of the mouth of a patient or by an operator to observe the conditions of his or her own teeth or gums. Electric toothbrushes are also widely used domestically.

Such a video scope for local image pickup and an electric toothbrush must be easy to handle so as to be held and operated with one hand.

The video scope and the electric toothbrush are conventionally used independently of each other. That is, it has been necessary to use the video scope to observe the teeth or gums for tartar or some bits of food stuck thereto, brush relevant portions with the electric toothbrush, and use the video scope to check how these portions have been brushed. In this case, it has been difficult to view images to check whether the site observed with the video scope correspond to the site to be brushed with the toothbrush.

Additionally, since a brushing operation is normally performed in a limited space such as a washroom, it is often difficult to set a space in a general home for installing a display section for displaying images from the video scope.

Further, the video scope is desirably cordless because complicated operations such as re-holding and rotation of the video scope or the toothbrush are required to fully observe and brush all the teeth.

BRIEF SUMMARY OF THE INVENTION

Object of the Invention

In view of these points, it is an object of the present invention to provide a tooth brushing device with a video scope that enables a user to brush his or her teeth while actually viewing images to check whether a site observed with the video scope correspond to a site to be brushed with a toothbrush.

SUMMARY OF THE INVENTION

One aspect of the present invention is a tooth brushing device with a video scope comprising:
 a video scope having image forming means for forming an image from light from an object, an image pickup element for converting the light formed into the image by means of said image forming means, into an electric signal, and a first handle means held by an operator;
 a toothbrush having a brush section and a second handle section held by the operator; and
 a display section for displaying the image picked up by said video scope, wherein:
 said first handle section and said second handle section are integrated together, and
 said image forming means is partly arranged where a tooth is imaged by said video scope when said operator brushes the tooth.

Another aspect of the present invention is the tooth brushing device with a video scope, wherein said image forming means is partly arranged on a rear side of a part of said brush section having a brush transplanted thereon.

Still another aspect of the present invention is the tooth brushing device with a video scope, comprising illumination means for illuminating the object.

Still yet another aspect of the present invention is the tooth brushing device with a video scope, wherein said tooth brush has a predetermined optical cavity portion such that light from said object is incident on said image forming means through said optical cavity portion.

A further aspect of the present invention is the tooth brushing device with a video scope, wherein said optical cavity portion is arranged in said brush section.

A still further aspect of the present invention is the tooth brushing device with a video scope, wherein said optical cavity portion is formed in an intermediate portion between said brush section of said tooth brush and said second handle section.

A yet further aspect of the present invention is the tooth brushing device with a video scope, wherein illumination light illuminates said object through said optical cavity portion.

A still yet further aspect of the present invention is the tooth brushing device with a video scope, wherein said optical cavity portion is formed in said brush section and in an intermediate portion between said brush section and the second handle section,
 light from said object is incident on said image forming means through said optical cavity portion in one of said brush section and said intermediate section, and
 the illumination light illuminates said object through the other of said brush section and said intermediate section.

An additional aspect of the present invention is the tooth brushing device with a video scope, wherein said video scope picks up an image in a manner such that a tip of said brush section is located at an end of the picked-up image.

A still additional aspect of the present invention is the tooth brushing device with a video scope, wherein said toothbrush is an electric toothbrush.

A yet additional aspect of the present invention is the tooth brushing device with a video scope, wherein at least said brush section of said electric toothbrush is movable independently of said first handle section.

A still yet additional aspect of the present invention is the tooth brushing device with a video scope, wherein said picked-up image is transmitted to said display section by means of a predetermined electric wave.

A supplementary aspect of the present invention is the tooth brushing device with a video scope, wherein said display section is arranged in a charger for charging said electric toothbrush or in a holder for holding said first handle section and said second handle section while the device is not in use.

A supplementary aspect of the present invention is the tooth brushing device with a video scope, wherein said video scope has a transmission window for transmitting said light between said image forming means and said object, and the device comprises removal means for removing extraneous matters to said transmission window.

A still supplementary aspect of the present invention is the tooth brushing device with a video scope, wherein said optical cavity portion has a transparent member for transmitting light.

A yet supplementary aspect of the present invention is the tooth brushing device with a video scope, wherein said transparent member has at least its surface facing said object subjected to hydrophilic treatment or has an attachment removing means on said surface for removing extraneous matters therefrom.

A still yet supplementary aspect of the present invention is a tooth brushing device with a video scope comprising:

a video scope having a transmission window for transmitting light from an object, image forming means for forming an image from the light from said object which has been transmitted through said transmission window, an image pickup element for converting the light formed into the image by means of said image forming means, into an electric signal, and a first handle means held by an operator;

a toothbrush having a brush section and a second handle section held by the operator; and a removal means for removing extraneous matters from said transmission window, wherein:
said first handle section and said second handle section are integrated together.

Another aspect of the present invention is a tooth brushing device with a video scope comprising:

a video scope having a transmission window for transmitting light from an object, image forming means for forming an image from the light from said object which has been transmitted through said transmission window, an image pickup element for converting the light formed into the image by means of said image forming means, into an electric signal, and a first handle means held by an operator; and a toothbrush having a transparent portion for transmitting the light from said object, a brush section, and a second handle section held by the operator, wherein:
said transparent portion has at least its surface facing said object subjected to hydrophilic treatment or has a first removal means on said surface for removing extraneous matters therefrom,
said first handle section and said second handle section are integrated together,
said transparent portion is arranged between said brush section of said toothbrush and said second handle section or in said brush section of said toothbrush, and
said transmission window is arranged so as to transmit therethrough the light from said object which has been transmitted through said transparent portion.

Still another aspect of the present invention is the tooth brushing device with a video scope, wherein image pickup conditions for said video scope can be switched so as to pick up a clear image of said object whether said image forming means forms an image from the light from said object which has or has not been transmitted, through said transparent portion.

Yet still another aspect of the present invention is the tooth brushing device with a video scope, comprising second removal means for removing extraneous matters from said transmission window.

Still another aspect of the present invention is the tooth brushing device with a video scope, wherein said removal means is injection means for injecting a liquid and/or a gas.

Still another aspect of the present invention is the tooth brushing device with a video scope, wherein said first removal means and/or said second removal means are/is injection means for injecting a liquid and/or a gas.

Yet another aspect of the present invention is the tooth brushing device with a video scope, wherein said removal means is wiping means for wiping extraneous matters off from said transmission window.

Still yet another aspect of the present invention is the tooth brushing device with a video scope, wherein said first removal means and/or said second removal means are/is wiping means for wiping extraneous matters off from said transmission window and/or said transparent portion.

A further aspect of the present invention is the tooth brushing device with a video scope, wherein said removal means is vibration means for vibrating said transmission window.

A still further aspect of the present invention is the tooth brushing device with a video scope, wherein said first removal means and/or said second removal means are/is vibration means for vibrating said transmission window and/or transparent portion.

A yet further aspect of the present invention is the tooth brushing device with a video scope, comprising control means for controlling operations of said removal means, said control means being arranged in said first handle section and second handle section which are integrated together.

A still yet further aspect of the present invention is the tooth brushing device with a video scope, comprising control means for controlling operations of said first removal means and/or said second removal means, said control means being arranged in said first handle section and second handle section which are integrated together.

A further aspect of the present invention is the tooth brushing device with a video scope, wherein said toothbrush is an electric toothbrush and comprises:

drive means for driving the brush section of said electric toothbrush, said drive means being arranged in said first handle section and second handle section which are integrated together, said drive means being also capable of controlling operations of said removal means.

A still further aspect of the present invention is the tooth brushing device with a video scope, wherein said toothbrush is an electric toothbrush and comprises:

drive means for driving the brush section of said electric toothbrush, said drive means being arranged in said first handle section and second handle section which are integrated together, said drive means being also capable of controlling operations of said first removal means and/or said second removal means.

A yet further aspect of the present invention is a tooth brushing device with a video scope comprising:

a video scope having a transmission window for transmitting light from an object, image forming means for forming an image from the light from said object which has been transmitted through said transmission window, an image pickup element for converting the light formed into the image by means of said image forming means, into an electric signal, and a first handle means held by an operator; and a toothbrush having a brush section, a through-hole, and a second handle section held by the operator, wherein:
said first handle section and said second handle section are integrated together,
said through-hole is covered by a transparent member, and
said transmission window transmits the light transmitted through said transparent member while said image forming means forms the image from the light from said object which has been transmitted through said transparent member and said transmission window.

A still yet further aspect of the present invention is the tooth brushing device with a video scope, wherein said transparent member is a transparent film or plate.

An additional aspect of the present invention is the tooth brushing device with a video scope, wherein said through-hole is formed in said brush section, and said transparent film is arranged in a portion adjoining an outer surface of said brush section of said video scope.

A still additional aspect of the present invention is the tooth brushing device with a video scope, comprising illumination means for illuminating the object.

A yet additional aspect of the present invention is the tooth brushing device with a video scope, wherein the illumination light is applied to said object through said transparent portion or said transparent member.

A still yet additional aspect of the present invention is the tooth brushing device with a video scope, wherein said transmission window is subjected to water-repellent or hydrophilic treatment that allows visible light to be transmitted therethrough.

A supplementary aspect of the present invention is the tooth brushing device with a video scope, wherein all or part of said transmission window, and said transparent portion is subjected to water-repellent or hydrophilic treatment that allows visible light to be transmitted therethrough.

A still supplementary aspect of the present invention is the tooth brushing device with a video scope, wherein all or part of said transmission window and said transparent member is subjected to water-repellent or hydrophilic treatment that allows visible light to be transmitted therethrough.

A yet supplementary aspect of the present invention is the tooth brushing device with a video scope, wherein said water-repellent treatment uses a dimethyl silicon-based organic polymer water-repellent treatment agent or a silane coupling agent having a straight alkyl chain.

DESCRIPTION OF SYMBOLS

| | |
|---|---|
| 1 | Brush |
| 2 | Head portion |
| 3 | Neck portion |
| 4 | Cavity portion |
| 5 | Cavity portion |
| 6 | Toothbrush base |
| 7, 105 | Handle sections |
| 8 | CCD unit |
| 9 | Objective lens |
| 10 | Prism mirror |
| 11 | White LED |
| 12, 14, 113 | Video scope head portion |
| 13, 107 | Video scope base |
| 15, 16 | Light guide |
| 106 | Control switch |
| 112 | Optical window (transmission window) |
| 114 | Pipe |
| 115 | Nozzle |

DETAILED DESCRIPTION OF THE PREFERRED EMBODIMENTS

Embodiments of the present invention will be described below with reference to the drawings.

Embodiment 1

Figure 1:
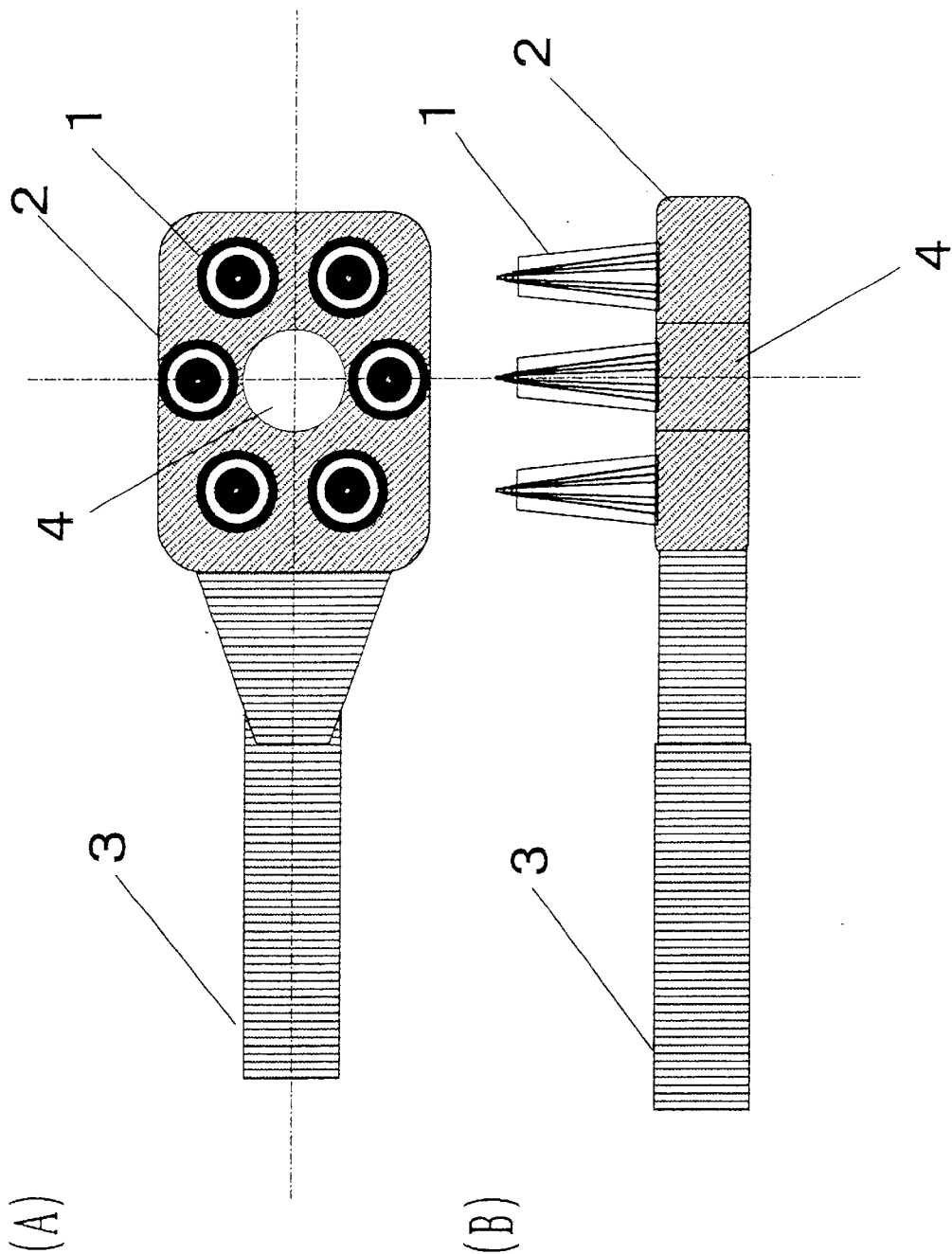
FIG. 1(A) is a top view showing the configuration of a main body of a tooth brushing device with a video scope according to Embodiment 1 of the present invention.
FIG. 1(B) is a side view of a tooth brush according to the embodiment shown in FIG. 1(A)

FIGS. 1(A) and 1(B) show a toothbrush of a main body of a tooth brushing device with a video scope according to Embodiment 1 of the present invention, the toothbrush having a cavity portion in a head portion with a brush transplanted thereon. In FIGS. 1(A) and 1(B), reference numeral 1 denotes the brush, reference numeral 2 denotes the head portion with the brush transplanted thereon, and reference numeral 3 denotes a neck portion for supporting the head portion 2. Reference numeral 4 denotes the cavity portion formed in the head portion 2 and shaped like a cylinder having a central axis in a direction in which the brush 1 extends.

Figure 4:
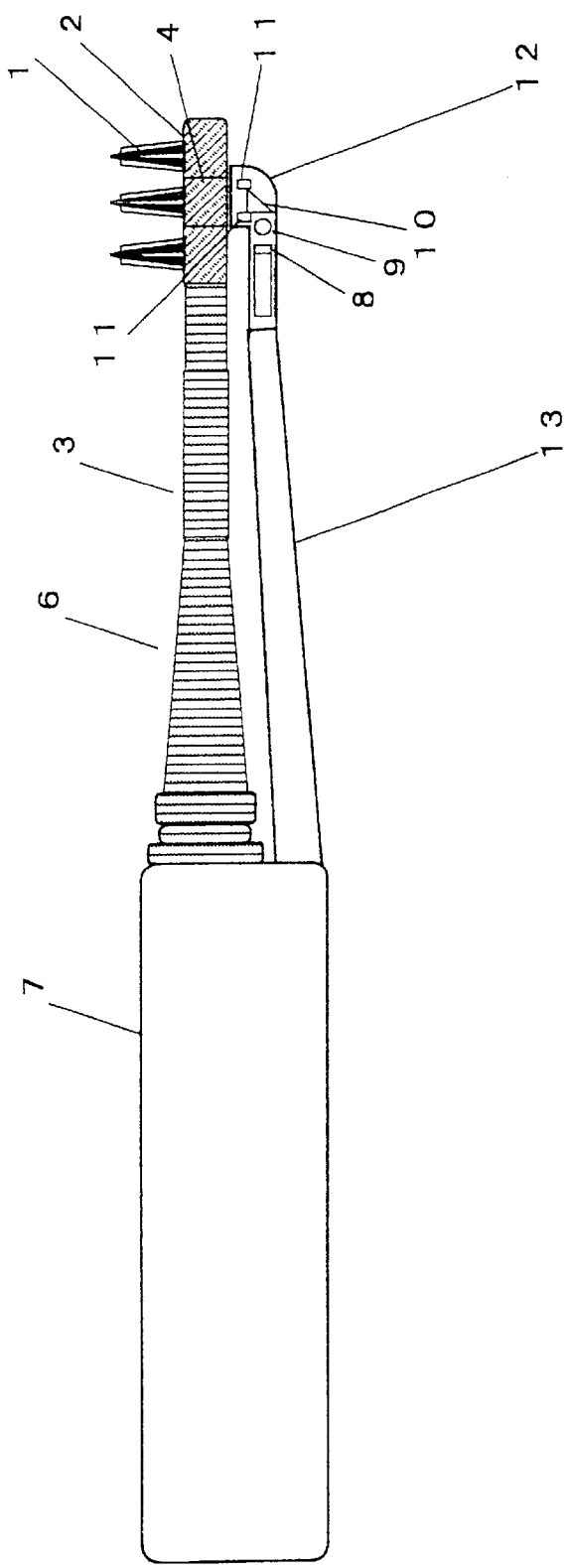
FIG. 4 is aside view of the main body of the tooth brushing device with the video scope according to Embodiment 1 of the present invention.

FIG. 4 is a side view of the main body of the tooth brushing device with the video scope according to Embodiment 1 of the present invention using the tooth brush shown in FIGS. 1(A) and 1(B). Reference numerals 1 to 4 in FIG. 4 denote the same components as reference numerals 1 to 4 in FIGS. 1(A) and 1(B) Reference numeral 6 denotes a base located between the neck portion 3 and a handle section 7 to transmit power or the like. A brushing operation is performed by, for example, reciprocating the entire toothbrush using the base 6 or rotating or rotationally reciprocating the brush 1 using a power transmission mechanism provided in the base 6, neck portion 3, and head portion 2. The handle section 7 internally has a power supply, motor for driving the tooth brush, and a signal processing circuit, an image transmitting circuit, and an illumination control circuit for the video scope.

Reference numeral 8 denotes a CCD unit having a CCD arranged at a tip thereof and acting as a solid image pickup element, and a drive circuit and signal processing circuit substrate disposed in each terminal. Reference numeral 9 denotes an objective lens for forming an image on a light receiving surface of the CCD of the CCD unit 8. Reference numeral 10 denotes a prism mirror for reflecting image pickup light. An iris is provided between the objective lens 9 and the prism mirror 10 to adjust the angle of visibility and the focal depth but is omitted from this figure.

The CCD unit 8, the objective lens 9, and the prism mirror 10 constitute an image pickup system. Image pickup light is incident on this image pickup system through the cavity portion 4. Reference numeral 11 denotes a white LED for illuminating an object, and illumination light from the white LED 11 also illuminates the object through the cavity portion 4. The image pickup system and the illumination means constitute a head portion 12 of the video scope. Reference numeral 13 denotes a video scope base through which the video scope head portion 12 is installed on the handle section 7. Electric wiring is provided in the video scope base 13 for supplying various signals and power but is omitted from this figure.

Figure 8:
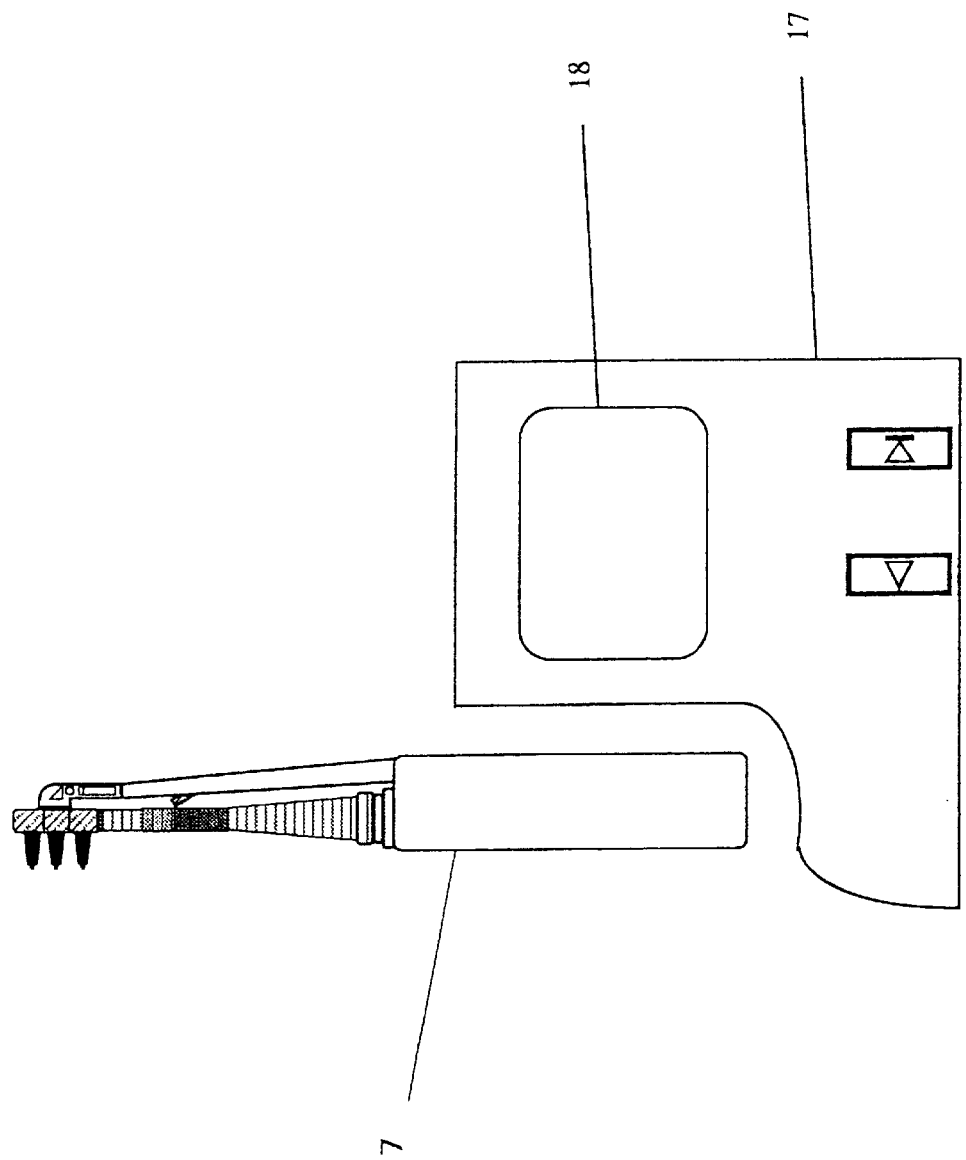
FIG. 8 is a general view of a tooth brushing device with a video scope including the main body of the tooth brushing device with the video scope according to each of the embodiments of the present invention as well as a charger and installer.

An image picked up by the video scope is transmitted over a predetermined electric wave and displayed on a display section 18, shown in FIG. 8. FIG. 8 shows the integrated video scope and toothbrush shown in FIG. 4 (that is, the main body of the tooth brushing device with the video scope) and the display section 18 for displaying an image picked up by the video scope. That is, FIG. 8 is a general view of the tooth brushing device with the video scope according to Embodiment 1 of the present invention.

Reference numeral 7 in FIG. 8 denotes the same handle section as reference numeral 7 in FIG. 4. Reference numeral 17 denotes a charger and a installer for installing the toothbrush with the video scope with the handle section 7 facing downward and includes a display section 18 for displaying the image picked up by the video scope.

The handle section 7 has a transmission circuit integrated thereinto for transmitting the picked-up image. In addition, the charger and installer 17 has a reception circuit for receiving the transmitted image as well as a display circuit, both circuits being integrated thereinto.

As described above, when the toothbrush section with the video scope is cordless and transmits an image to the charger and installer 17 with the display section 18, a user can handle the device more easily and can save more space. Consequently, this device can be spread to many homes and the like.

Next, the operation of brushing the teeth while actually observing them using the toothbrush section with the video scope according to this embodiment will be explained. Portions of the device beyond the toothbrush base 6 and the video scope base 13 advance into the mouth to pick up images of the teeth and the gums while performing the brushing operation. When the toothbrush is placed so as to brush a particular tooth, the angle of visibility or the focal length or depth of the image pickup system or the illumination angle or intensity of the illumination means is adjusted so that a tip portion of the brush 1 is located in a peripheral portion or a corner of the picked-up image while the teeth to be brushed is located in a central portion thereof.

As described above, by imaging and illuminating the tooth through the cavity portion 4 of the head portion 2 of the toothbrush and adjusting the image pickup system and the illumination means so that the tip portion of the brush 1 is located in a peripheral portion or a corner of the picked-up image while the teeth to be brushed is located in a central portion thereof, the brushing operation can be preformed while actually viewing images to check whether the site observed with the video scope correspond to the site to be brushed. In addition, since the toothbrush base 6 and the video scope base 13 are separately fixed to the handle section 7, images can be picked up during a reciprocating operation of the toothbrush. This device is therefore very practically effective.

That is, while viewing the inside of the mouth using the video scope, the tooth being viewed can be reliably brushed, so that the brushing operation can be efficiently and reliably performed without missing sites to be brushed.

Embodiment 2

Figure 2:
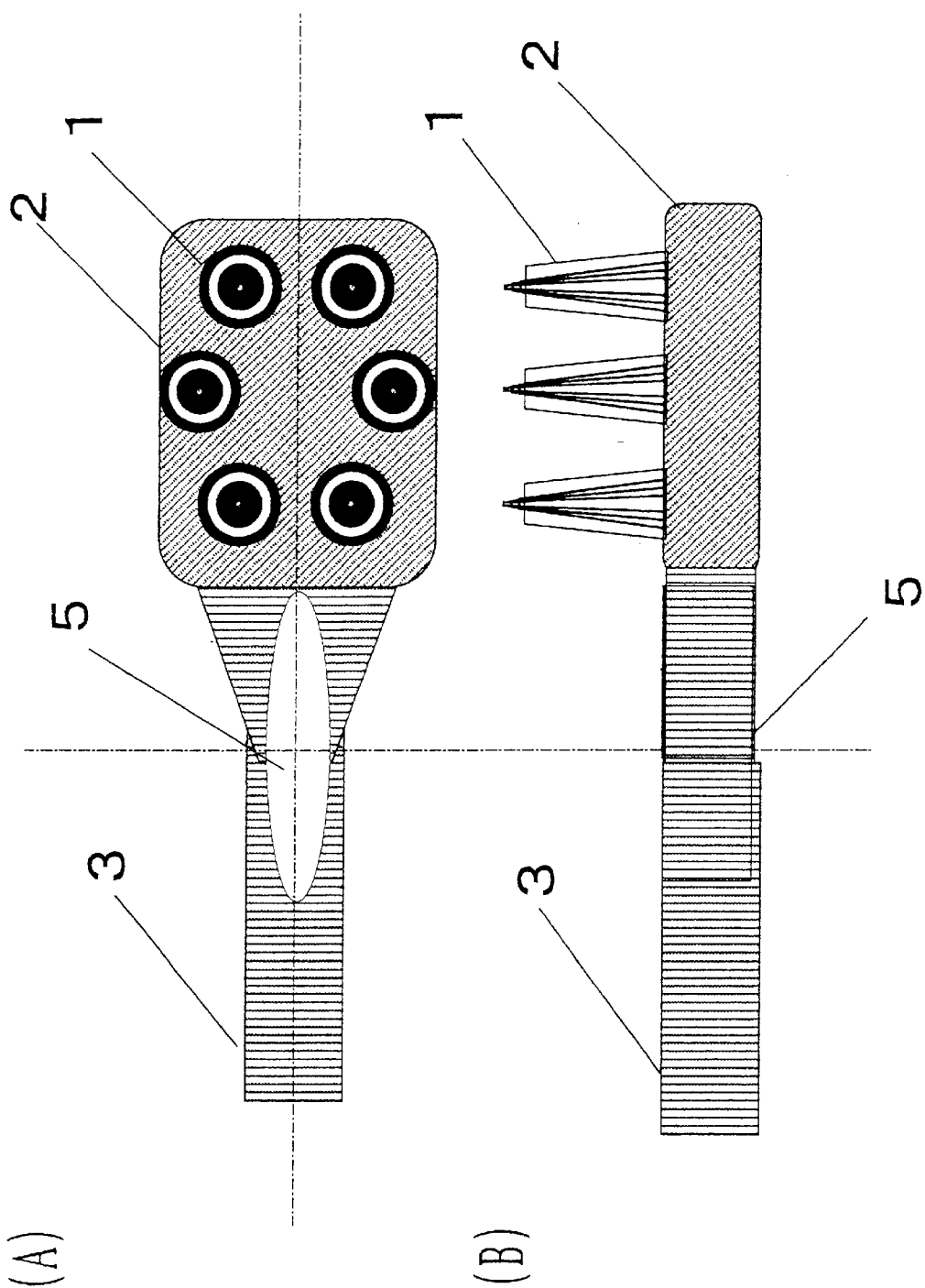
FIG. 2(A) is a top view showing the configuration of a main body of a tooth brushing device with a video scope according to Embodiment 2 of the present invention.
FIG. 2(B) is a side view of a tooth brush according to the embodiment shown in FIG. 2(A)

FIGS. 2(A) and 2(B) show a toothbrush of a main body of a tooth brushing device with a video scope according to Embodiment 2 of the present invention, the toothbrush having a cavity portion in a neck portion supporting a head portion. In FIGS. 2(A) and 2(B), reference numerals 1, 2, and 3 denote the same components as reference numerals 1, 2, and 3 in FIGS. 1(A) and 1(B). Reference numeral 5 denotes the cavity portion formed in the neck portion 3 and shaped like an elliptic cylinder having a central axis in a direction in which the brush 1 extends.

Figure 5:
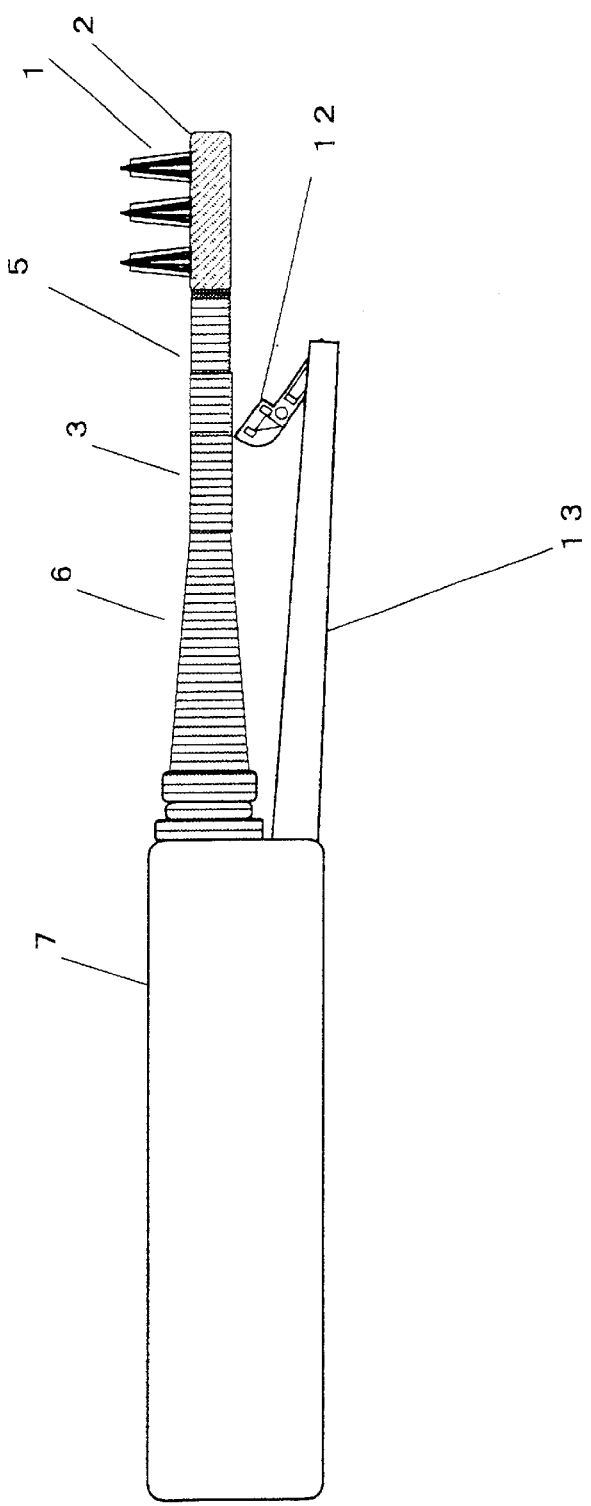
FIG. 5 is a side view of the main body of the tooth brushing device with the video scope according to Embodiment 2 of the present invention.

FIG. 5 is a side view of the main body of the tooth brushing device with the video scope according to Embodiment 2 of the present invention using the tooth brush shown in FIGS. 2(A) and 2(B). Reference numerals 1 to 3 and 5 in FIG. 5 denote the same components as reference numerals 1 to 3 and 5 in FIGS. 2(A) and 2(B). Reference numerals 6, 7, 12, and 13 also denote the same components as reference numerals 6, 7, 12, and 13 in FIG. 4, but the head portion 12 of the video scope is arranged in a manner different from that in FIG. 4. That is, the video scope head portion 12 is arranged so that image pickup light is incident on the image pickup system through the cavity portion 5 formed in the neck portion 3 and illumination light also illuminates the object through the cavity portion 5. This is the point at which Embodiment 2 differs from Embodiment 1. Accordingly, the other points are the same as those of Embodiment 1 and description thereof is thus omitted.

Next, the operation of brushing the teeth while actually observing them using the toothbrush section with the video scope according to this embodiment will be explained. Portions of the device beyond the toothbrush base 6 and the video scope base 13 advance into the mouth to pick up images of the teeth and the gums while performing the brushing operation. When the toothbrush is placed so as to brush a particular tooth, the angle of visibility or the focal length or depth of the image pickup system or the illumination angle or intensity of the illumination means is adjusted so that the tip portion of the brush 1 is located in an end of the picked-up image while the teeth to be brushed is located in the remaining part thereof.

As described above, by imaging and illuminating the tooth through the cavity portion 5 of the neck portion 3 of the toothbrush and adjusting the image pickup system and the illumination means so that the tip portion of the brush 1 is located in an end of the picked-up image while the teeth to be brushed is located in the remaining part thereof, the brushing operation can be preformed while actually viewing images to check whether the site observed with the video scope correspond to the site to be brushed. In addition, since the toothbrush base 6 and the video scope base 13 are separately fixed to the handle section 7, images can be picked up during a reciprocating operation of the toothbrush. This device is therefore very practically effective. Additionally, according to this embodiment, the cavity portion 5 formed in the neck portion 3 provides a higher degree of freedom than that in Embodiment 1.

Embodiment 3

Figure 3:
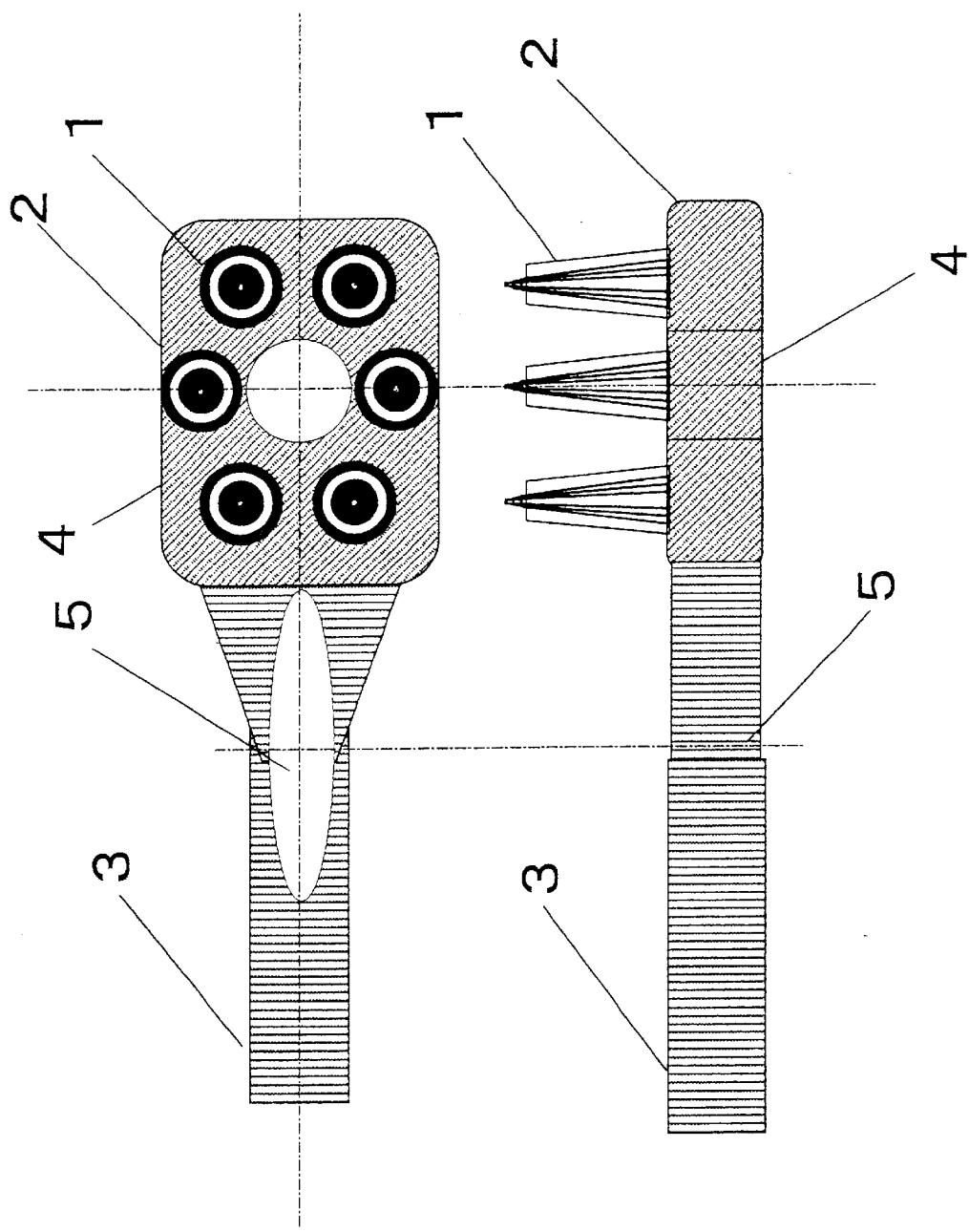
FIG. 3(A) is a top view showing the configuration of a main body of a tooth brushing device with a video scope according to Embodiments 3 and 4 of the present invention.
FIG. 3(B) is a side view of a tooth brush according to the embodiment shown in FIG. 3(A)

FIGS. 3(A) and 3(B) show a toothbrush of a main body of a tooth brushing device with a video scope according to Embodiment 3 of the present invention, the toothbrush having a cavity portion in a head portion with a brush transplanted thereon and in a neck portion supporting the head portion. In FIGS. 3(A) and 3(B), reference numerals 1, 2, 3, 4, and 5 denote the same components as reference numerals 1, 2, 3, 4, and 5 in FIGS. 1(A) and 2(B).

Figure 6:
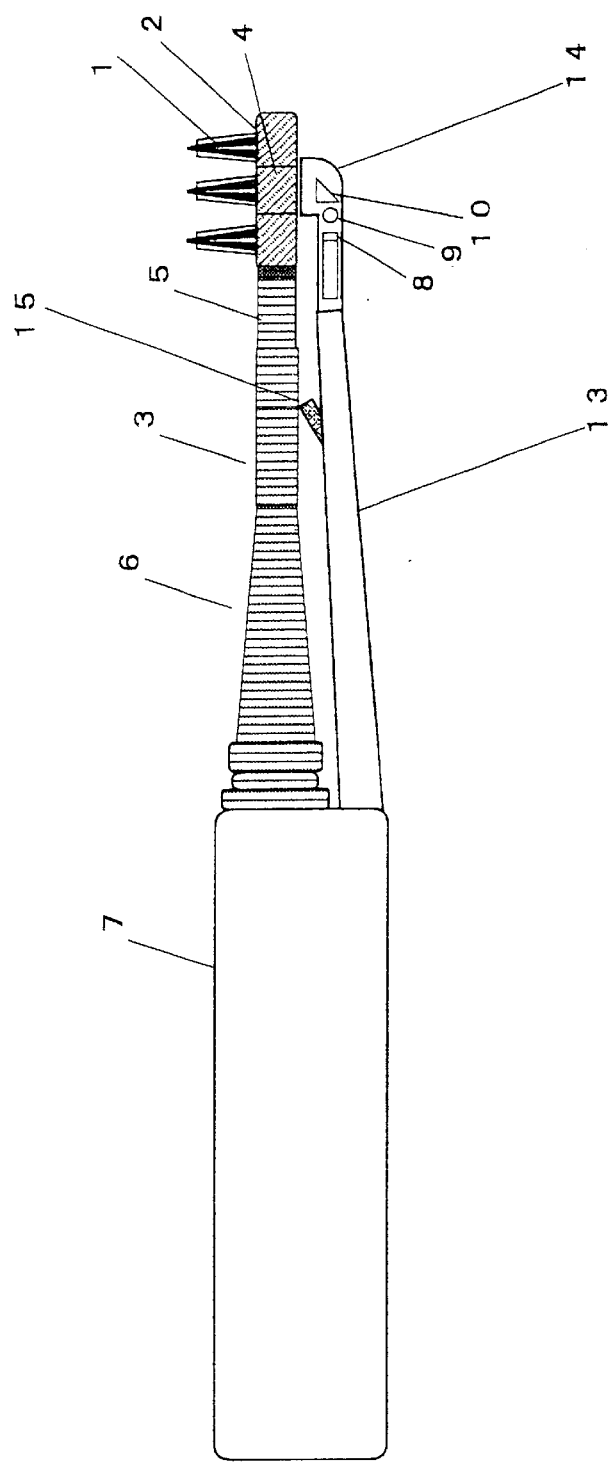
FIG. 6 is a side view of the main body of the tooth brushing device with the video scope according to Embodiment 3 of the present invention.

FIG. 6 is a side view of the main body of the tooth brushing device with the video scope according to Embodiment 3 of the present invention using the tooth brush shown in FIGS. 3(A) and 3(B). Reference numerals 1 to 5 in FIG. 6 denote the same components as reference numerals 1 to 5 in FIGS. 3(A) and 3(B). Reference numerals 6, 7, and 13 in FIG. 6 denote the same components as reference numerals 6, 7, and 13 in FIG. 4. Reference numeral 14 denotes the head portion of the video scope, which differs from the head portion 12 of the video scope shown in FIG. 4 in that it does not include the white LED 11, the illumination means. Image pickup light is incident on the head portion 14 of the video scope through the cavity portion 4 formed in the head portion 2 of the toothbrush. Reference numeral 15 denotes a light guide comprising a material such as a transparent acrylic resin and acting as an illumination means for projecting illumination light on the object through the cavity portion 5 formed in the neck portion 3. The light guide 15 has a converging means or a light source arranged opposite to an emitting side thereof.

As described above, this embodiment differs from Embodiments 1 and 2 in that it includes the cavity portions 4 and 5 such that when light from the cavity portion 5 is applied to the object, light reflected therefrom is received by the CCD unit 8 through the cavity portion 4 via the prism mirror 10 and the objective lens 9. The other points are the same as those of Embodiment 1 or 2 and description thereof is thus omitted.

Next, the operation of brushing the teeth while actually observing them using the toothbrush section with the video scope according to this embodiment will be explained. Portions of the device beyond the toothbrush base 6 and the video scope base 13 advance into the mouth to pick up images of the teeth and the gums while performing the brushing operation. When the toothbrush is placed so as to brush a particular tooth, the angle of visibility or the focal length or depth of the image pickup system or the angle or illumination intensity of the light guide 15, the illumination means, is adjusted so that the tip portion of the brush 1 is located in a peripheral portion or a corner of the picked-up image while the teeth to be brushed is located in a central portion thereof.

As described above, by imaging the tooth through the cavity portion 4 of the head portion 2 of the toothbrush, illuminating it through the cavity portion 5 of the neck portion 3 of the toothbrush, and adjusting the image pickup system and the illumination means so that the tip portion of the brush 1 is located in an end of the picked-up image while the teeth to be brushed is located in the remaining part thereof, the brushing operation can be preformed while actually viewing images to check whether the site observed with the video scope correspond to the site to be brushed. In addition, since the toothbrush base 6 and the video scope base 13 are separately fixed to the handle section 7, images can be picked up during a reciprocating operation of the toothbrush. This device is therefore very practically effective. Further, according to this embodiment, the image pickup system and the illumination means are separated from each other, thereby easily preventing the illumination light from directly entering the image pickup system.

Embodiment 4

Figure 7:
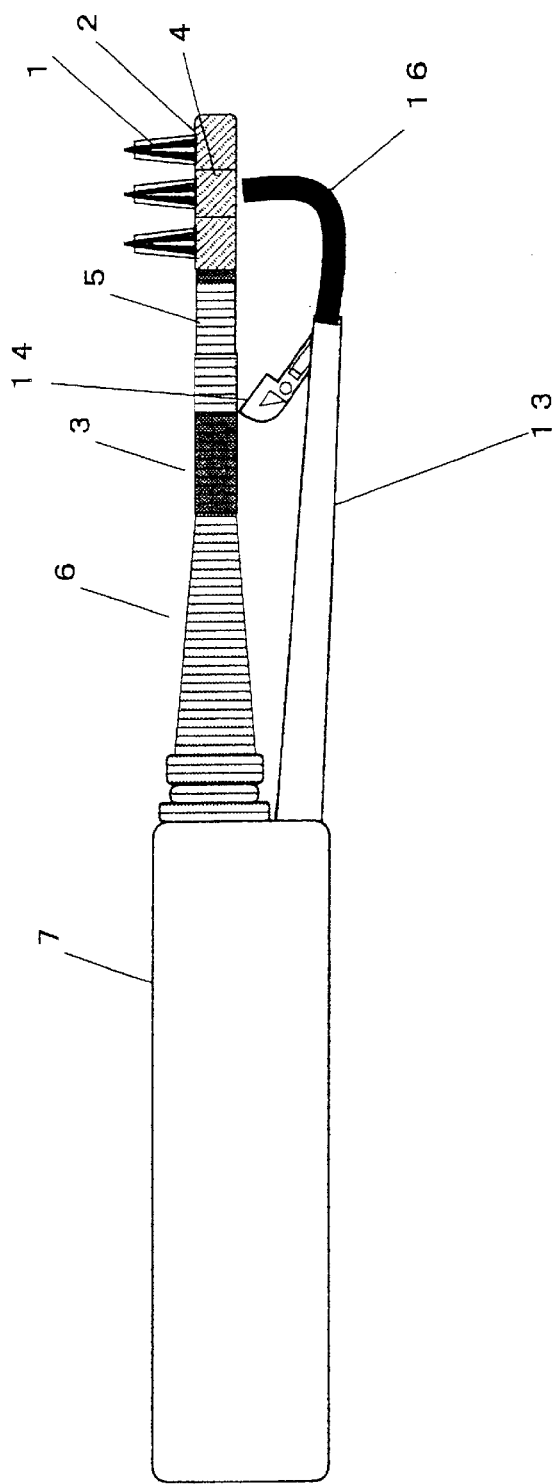
FIG. 7 is a side view of the main body of the tooth brushing device with the video scope according to Embodiment 4 of the present invention.

FIG. 7 is a side view of the main body of the tooth brushing device with the video scope according to Embodiment 4 of the present invention using the tooth brush shown in FIGS. 3(A) and 3(B). Reference numerals 1 to 7 in FIG. 7 denote the same components as reference numerals 1 to 7 in FIG. 6. Reference numerals 13 and. 14 in FIG. 7 also denote the same components as reference numerals 13 and 14 in FIG. 6, but the head portion 14 of the video scope is arranged in a manner different from that in FIG. 6. That is, the head portion 14 is arranged so that image pickup light is incident on the image pickup system through the cavity portion 5 formed in the neck portion 3. Reference numeral 16 denotes a light guide comprising a material such as a transparent acrylic resin similarly to reference numeral 15 and acting as an illumination means for projecting illumination light on the object through the cavity portion 4 formed in the head portion 2. The light guide 16 has a converging means or a light source arranged opposite to an emitting side thereof. The portions of this device other than the arrangement position of the head portion 14 of the video scope as well as the light guide 16 are the same as those in the above described Embodiment 3, and description thereof is thus omitted.

Next, the operation of brushing the teeth while actually observing them using the toothbrush section with the video scope according to this embodiment will be explained.

Portions of the device beyond the toothbrush base 6 and the video scope base 13 advance into the mouth to pick up images of the teeth and the gums while performing the brushing operation. When the toothbrush is placed so as to brush a particular tooth, the angle of visibility or the focal length or depth of the image pickup system or the angle or illumination intensity of the light guide 16, the illumination means, is adjusted so that the tip portion of the brush 1 is located in an end of the picked-up image while the teeth to be brushed is located in the remaining part thereof.

As described above, by imaging the tooth through the cavity portion 5 of the neck portion 3 of the toothbrush, illuminating it through the cavity portion 4 of the head portion 2 of the toothbrush, and adjusting the image pickup system and the illumination means so that the tip portion of the brush 1 is located in an end of the picked-up image while the teeth to be brushed is located in the remaining part thereof, the brushing operation can be preformed while actually viewing images to check whether the site observed with the video scope correspond to the site to be brushed.

In addition, since the toothbrush base 6 and the video scope base 13 are separately fixed to the handle section 7, images can be picked up during a reciprocating operation of the toothbrush. This device is therefore very practically effective. Further, according to this embodiment, the image pickup system and the illumination means are separated from each other, thereby easily preventing the illumination light from directly entering the image pickup system. Additionally, in contrast to Embodiment 3, the light guide 16, the illumination means the weight of which can be educed more easily than that of the image pickup means, is arranged at the tip portion of the video scope, thereby reducing an inertia moment to allow the user to operate the device comfortably. Moreover, the light guide 16, the illumination means the size of which can be educed more easily than that of the image pickup means, is arranged at the tip portion of the video scope, thereby enabling the size of the entire tip portion including the toothbrush to be reduced. Therefore, this embodiment is advantageous in observing or brushing the back teeth and their peripheries.

As described above, the tooth brushing device with the video scope according to each of the above embodiments enables the user to observe or check the inside of the mouth while simultaneously performing a maintenance operation such as tooth brushing. This device is thus very practically effective.

In the above described embodiments, the objective lens 9, the prism mirror 10, and the iris constitute an example of the image forming means of the video scope of the tooth brushing device with the video scope according to the present invention. In addition, in the above described embodiments, the handle section 7 constitutes an example of the first handle section of the video scope and the second handle section of the toothbrush.

Further, FIG. 8, which has been described for Embodiment 1, is a general view of the tooth brushing device with the video scope according to Embodiment 1, but it is also a general view of each of the tooth brushing devices with the video scopes according to Embodiments 2 to 4. Moreover, the display section 18 shown in FIG. 8 need not necessarily be arranged in the charger and installer 17.

Additionally, in the above described embodiments, the image picked up by the video scope is transmitted to the display section 18 by electric wave, but the transmission medium is not limited to the electric wave.

In addition, in the above described embodiments, the toothbrush has been described as the electric toothbrush, but it need not be of this type. Further, if the toothbrush is electrically driven, it need not necessarily be of a charge type.

Moreover, in the above described embodiments, the video scope has the illumination means such as the white LED or the light guide, but the illumination means need not be provided.

Furthermore, the arrangement positions of the CCD unit 8, the motor for driving the toothbrush, the signal processing and image transmitting circuits for the video scope, and others in the above described embodiments are not limited to those shown in the figures or the above description.

In the above described embodiments, the optical cavity portion according to the present invention has been described as the through-hole, but the present invention is not limited to this but the cavity portion may be filled with a transparent resin or glass or the like or may be blocked by a transparent plate member. In short, the cavity portion may have any structure as long as light is transmitted therethrough.

Additionally, in the above embodiments, the head portion of the toothbrush is generally rectangular in a top view, but the present invention is not limited to this but the head portion may be, for example, circular.

Further, in Embodiment 2, the video scope head portion 12 extends in a fashion being bent from the tip portion of the video scope base 13 toward the handle section 7 as shown in FIG. 5, but the present invention is not limited to this but of course a configuration is possible in which the vide scope head portion extends toward the head portion 2 from the tip portion of a video scope base shorter than the video scope base 13 shown in FIG. 5 and receives light from the object through the elliptical cavity portion 5.

On the other hand, with the structure of the tooth brushing device with the video scope according to the above described embodiments, when images are picked up during the tooth brushing operation, bubbles, droplets, or tooth powders may stick to the optical window (transmission window) of the image forming means to hinder clear images from being obtained.

Thus, in view of this point, in the embodiments described below, a specific example of a tooth brushing device with a video scope will further be described which obtains clear images even during the tooth brushing operation by removing image pickup obstacles such as bubbles, droplets, or tooth powders which obstructs image pickup when such obstacles have stuck or are to stick to the optical window (transmission window) arranged on the object side of the image forming means or to the transparent portion of the video scope.

Embodiments of the present invention will be described below with reference to FIGS. 9 to 19.

Embodiment 5

Figure 9:
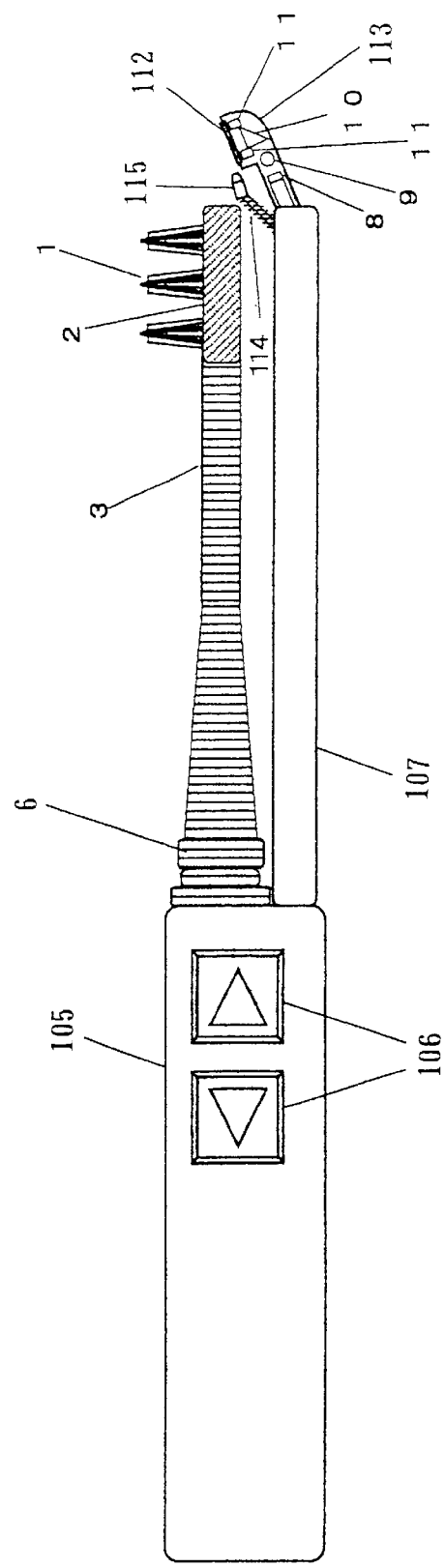
FIG. 9 is a side view of a main body of a tooth brushing device with a video scope according to Embodiment 5 of the present invention.

FIG. 9 is a side view of a main body of a tooth brushing device with a video scope according to Embodiment 5 of the present invention. In FIG. 9, reference numeral 1 denotes a brush, reference numeral 2 denotes a head portion with a brush transplanted thereon, and reference, numeral 3 denotes a neck portion for supporting the head portion 2. Reference numeral 6 denotes a base located between the neck portion 3 and a handle section 105 to transmit power or the like. A brushing operation is performed by, for example, reciprocating the entire toothbrush using the base 6 or rotating the brush 1 using a power transmission mechanism provided in the base 6, neck portion 3, and head portion 2.

The handle section 105 internally has a power supply, motor for driving the tooth brush, and a signal processing circuit, an image transmitting circuit, and an illumination control circuit for the video scope. The handle section 105 also has a control switch 106 for controlling operations of the toothbrush or injection of a liquid. The handle section 105 further has a video scope base 107 for supporting a head portion 113 of the video scope.

Reference numeral 8 denotes a CCD unit having a CCD arranged at a tip thereof and acting as a solid image pickup element, and a drive circuit and signal processing circuit substrate disposed in each terminal. Reference numeral 9 denotes an objective lens for forming an image on a light receiving surface of the CCD of the CCD unit 8. Reference numeral 10 denotes a prism mirror for reflecting image pickup light. An iris is provided between the objective lens 9 and the prism mirror 10 to adjust the angle of visibility and the focal depth but is omitted from this figure. The prism mirror 10, the iris, and the objective lens 9 constitute an image forming means.

Reference numeral 11 denotes a white LED for illuminating an object, and reference numeral 12 denotes an optical window (transmission window) comprising glass or the like to provide a waterproof function by closing the white LED while transmitting visible light so that light from the object can enter the prism mirror 10. The CCD unit 8 and the image forming means constitute an image pickup means. The image pickup system and the illumination means constitute a head portion 113 of the video scope. The video scope head portion 113 is attached to the handle section 105 via the video scope base 107, and electric wiring is provided in the video scope base 107 for supplying various signals and power but is omitted from this figure. The arrangement shown in FIG. 9 enables the tooth brushing operation to be performed while checking the target tooth through the video scope.

Reference numeral 115 denotes a nozzle that injects a liquid such as water which has been delivered through a pipe 114, onto the optical window 112. The injection of the liquid is controlled by a switch 106 provided in the handle section 105.

Portions of the device beyond the attachment (handle section) 105 and the video scope base 107 advance into the mouth to pick up images of the teeth and the gums while performing the brushing operation. When the toothbrush is placed so as to brush a particular tooth, the angle of visibility or the focal length or depth of the image pickup system or the illumination angle or intensity of the illumination means, is adjusted so that the tip portion of the brush 1 is located in an end of the picked-up image while the teeth to be brushed is located in the central portion thereof.

During the tooth brushing operation, bubbles or droplets are likely to occur and these bubbles or droplets or tooth powders may stick to the optical window 112 to hinder the image pickup. In this case, when the operator operates the switch 106, the liquid is injected onto the optical window 112 through the nozzle 115 to remove the extraneous matters such as the bubbles, droplets, and tooth powders therefrom. When a picked-up image or the like shows that all the extraneous matters have been removed and the operator then operates the control switch 106 to stop injecting the liquid, a clear image of the target tooth or gum is picked up again.

As described above, when the means for injecting the liquid onto the optical window 112 is provided and controlled by the operator and if bubbles, droplets, tooth powders, or the like stick to the optical window 112 to hinder the image pickup while the operator is performing the tooth brushing operation while actually viewing an image to check whether a site observed by the video scope corresponds to a site to be brushed by the tooth brush, then these extraneous matters can be removed. This enables the checking with a stable image even during the tooth brushing operation. This device is thus very practically effective.

Since the toothbrush base 6 and the video scope base 107 are separately fixed to the handle section 105, images can be picked up even while the toothbrush is reciprocating.

In addition, in the above described Embodiment 5, the liquid such as water is injected through the nozzle 115, but a gas such as air may be injected therethrough. In short, the nozzle 115 as the injection means allows the liquid or the gas to be injected therethrough to remove bubbles, droplets, tooth powders, or the like which have stuck or are to stick to the optical window 112.

Additionally, the nozzle 115 as the injection means in the above described Embodiment 5 may be arranged in the video scope as shown in FIG. 9 or for example, in the head portion 2 of the toothbrush. In short, the nozzle 115 as the injection means need not necessarily be arranged in the video scope.

Further, in the above described Embodiment 5, the control switch 106 provided in the handle section 105 has been described as the means for controlling the operation of the toothbrush and the injection of the liquid, but a means for controlling only the operation of the toothbrush and a means for controlling the injection of the liquid or the gas may be separately provided.

The image picked up by the video scope is transmitted over the predetermined electric wave and displayed on the display section 18 shown in FIG. 8, as in the above described embodiments. As described for FIG. 8, the toothbrush with the video scope according to this embodiment can be installed in the installer shown in this figure with the handle section 7 facing downward. The display section 18 and the installer in the embodiments described below are exactly the same as those described above and description thereof is thus omitted.

As described above, when the toothbrush section with the video scope is cordless and transmits an image to the charger and installer 17 with the display section 18, the user can handle the device more easily and can save more space. Consequently, this device can be spread to many homes or the like.

Embodiment 6

Figure 10:
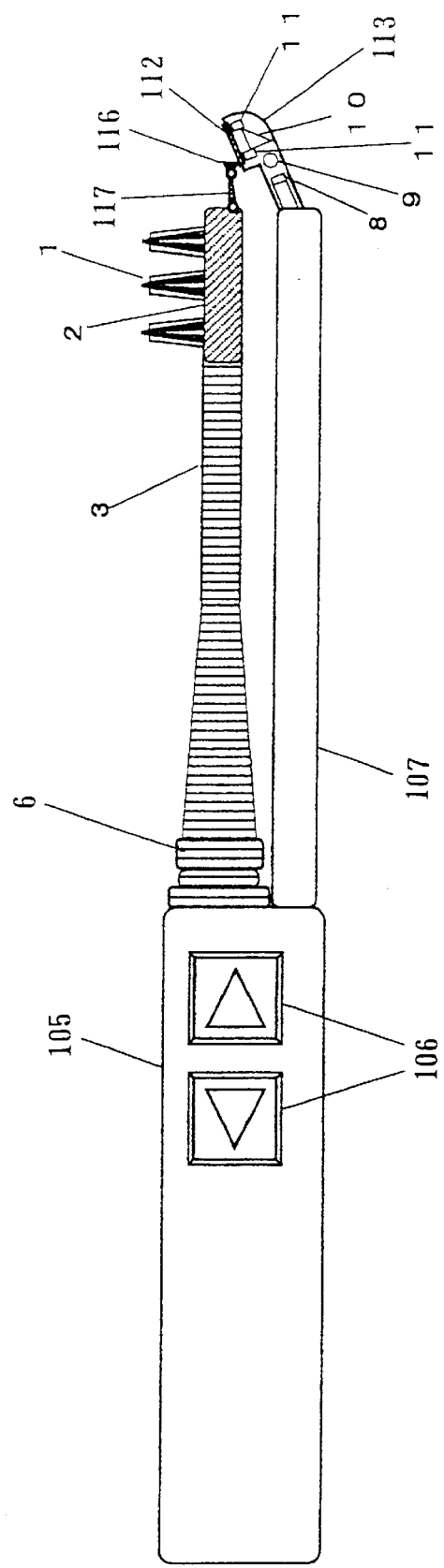
FIG. 10 is a side view of a main body of a tooth brushing device with a video scope according to Embodiment 6 of the present invention.

FIG. 10 is a side view of a main body of a tooth brushing device with a video scope according to Embodiment 6 of the present invention. Reference numerals 1 to 13 in FIG. 10 denote the same components as reference numerals 1 to 13 in FIG. 9 which are arranged in the same manner as those in FIG. 9.

In FIG. 10, reference numeral 116 denotes a rubber brush for removing bubbles, droplets, tooth powders, or the like from the optical window 112, the brush being coupled to the head portion 2 of the toothbrush via a coupling machine 117. When the toothbrush reciprocates for the tooth brushing operation, the brush 116 reciprocates over a surface of the optical window 112 to remove the bubbles, droplets, tooth powders, or the like therefrom.

As described above, when the means for wiping the optical window 112 is provided and if bubbles, droplets, or tooth powders stick to the optical window 112 to hinder the image pickup while the operator is performing the tooth brushing operation while actually viewing an image to check whether the site observed by the video scope corresponds to the site to be brushed by the tooth brush, then these extraneous matters can be removed. This enables the checking with a stable image even during the tooth brushing operation.

In this embodiment, the wiping means, that is, the brush 116 can be coupled to the head portion 2 of the toothbrush through the coupling machine 117, so that the operation of the toothbrush and the operation of the brush 116 can be simultaneously controlled using the control switch 106, that is, the drive means for the electric toothbrush. This device is thus very practically effective.

The operation of the brush 116 need not necessarily be linked with the operation of the toothbrush but, for example, the brush 116 may be arranged so as to wipe extraneous matters off from the optical window 112 while a means for controlling the operation of the brush 116 separately from the operation of the toothbrush may be provided in the handle section 105.

In addition, in the above described Embodiment 6, the brush 116 as the wiping means may be provided in the head portion 2 of the tooth brush as shown in FIG. 10 or for example, in the head portion 113 of the video scope. In short, the brush 116 as the wiping means need not necessarily be provided in the head portion 2 of the toothbrush.

Further, in the above described Embodiment 6, the brush 116 is made of rubber but its material is not limited to rubber. In short, the brush 116 may comprise any material as long as it can wipe extraneous matters off from the optical window 112 without substantially damaging it.

Embodiment 7

Figure 11:
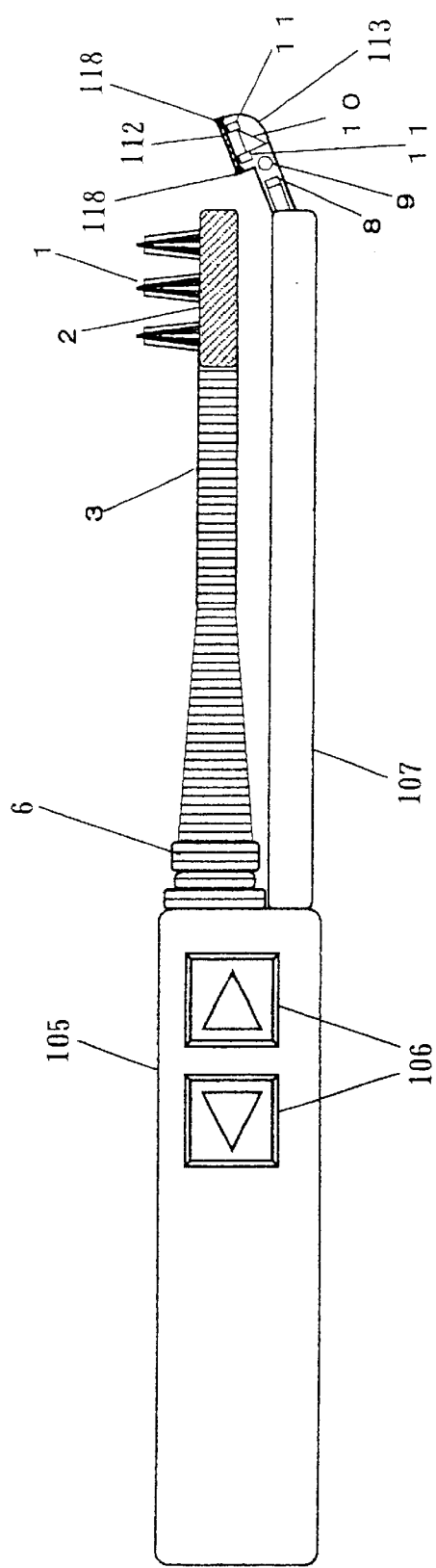
FIG. 11 is a side view of a main body of a tooth brushing device with a video scope according to Embodiment 7 of the present invention.
Figure 12:
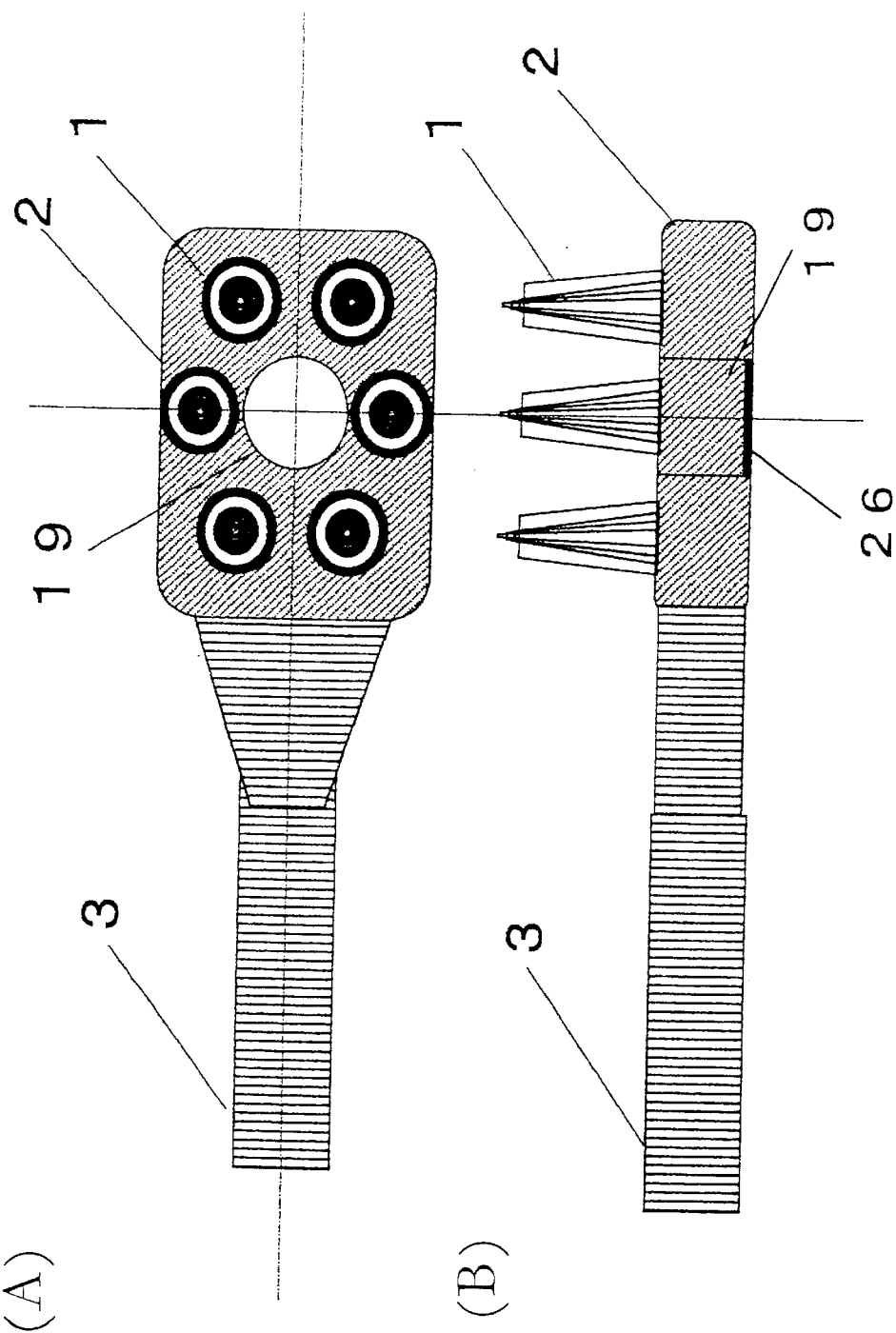
FIG. 12(A) is a top view showing the configuration of a main body of a tooth brushing device with a video scope according to Embodiment 8 of the present invention.
FIG. 12(B) is a side view of a tooth brush according to the embodiment shown in FIG. 12(A)

FIG. 11 is a side view of a main body of a tooth brushing device with a video scope according to Embodiment 7 of the present invention. Reference numerals 1 to 13 in FIG. 11 denote the same components as reference numerals 1 to 13 in FIG. 9 and are arranged in the same manner.

In FIG. 11, reference numeral 118 denotes a piezoelectric vibrator comprising barium titanate ceramics to slightly vibrate the optical window 112 at a frequency of 28 kHz. The piezoelectric vibrator 118 has its operation controlled by the control switch 106.

When bubbles, droplets, tooth powders, or the like which occur during the tooth brushing operation stick to the optical window 112 to hinder the image pickup, the operator operates the switch 106 to slightly vibrate the piezoelectric vibrator 118 to remove the bubbles, droplets, tooth powders, or the like from the optical window 112. Then, on confirming from an image or the like that the extraneous matters have been removed, the operator operates the control switch 106 to stop the minor vibration.

Higher effects are obtained by starting the minor vibration simultaneously with the start of the tooth brushing operation to hinder sticking of bubbles, droplets, tooth powders, or the like.

As described above, when the means for slightly vibrating the optical window 112 is provided and controlled by the operator and if bubbles, droplets, or tooth powders stick to the optical window 112 to hinder the image pickup while the operator is performing the tooth brushing operation while actually viewing an image to check whether the site observed by the video scope corresponds to the site to be brushed by the tooth brush, then these extraneous matters can be removed. Further, the injected liquid need not be supplied as in Embodiment 5, thereby eliminating the needs for cords. This enables the checking with a stable image even during the tooth brushing operation. This device is thus very practically effective.

In the above described Embodiment 7, the control switch 106 provided in the handle section 105 has been described as the means for controlling both the operation of the toothbrush and the vibration of the piezoelectric vibrator 118, but a means for controlling only the operation of the toothbrush and a means for controlling the vibration of the piezoelectric vibrator 118 may be separately provided.

Additionally, in the above described Embodiment 7, the piezoelectric vibrator 118 is formed of barium titanate ceramics, but may be formed of another material.

Furthermore, in the above described Embodiment 7, the piezoelectric 118 slightly vibrates the optical window 112 at a frequency of 28 kHz, but the frequency at which the optical window 112 is vibrated is not limited to 28 kHz. In short, the piezoelectric vibrator 118 has only to be able to vibrate the optical window 112.

Embodiment 8

FIGS. 12(A) and 12(B) show a toothbrush according to Embodiment 8 having a cavity portion in a head portion with a brush transplanted thereon.

In FIGS. 12(A) and 12(B), reference numeral 1 denote a brush, reference numeral 2 denotes a head portion with the brush 1 transplanted thereon, and reference numeral 3 denotes a neck portion for supporting the head portion 2. Reference numeral 19 denotes a cylindrical cavity having a central axis in a direction in which the brush extends and having a transparent film 26 stuck to a side of the head portion opposite to that with the brush 1 transplanted thereon, the film comprising polyvinylidene chloride. The transparent film 26 has a thickness of about 0.02 mm, blocks the cavity portion 19, and has its brush-1-side surface subjected to hydrophilic treatment that allows visible light to be transmitted therethrough.

The transparent film 26 is provided on the side of the head portion opposite to that with the brush 1 transplanted thereon because a smaller amount of bubbles or droplets stick as the distance between the transparent film 26 and the brush 1 is larger.

Figure 13:
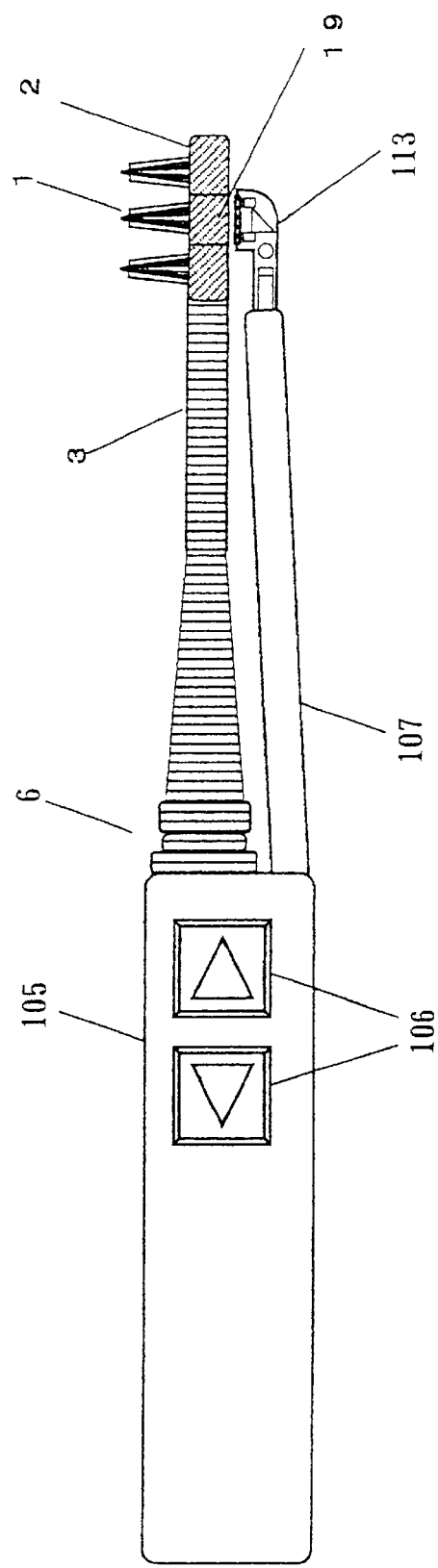
FIG. 13 is a side view of the main body of the tooth brushing device with the video scope according to Embodiment 8 of the present invention.

FIG. 13 is a side view of a main body of a tooth brushing device with a video scope using the toothbrush shown in FIGS. 12(A) and 12(B). Reference numerals 1 to 7 and 13 in FIG. 13 denote the same components as reference numerals 1 to 7 and 13 in FIG. 9.

Image pickup light is incident on the head portion 113 through the cavity portion 19 and the transparent film 26. Illumination light from the white LED housed in the head portion 113 also illuminates the object through the cavity portion 19. The transparent film 26 stuck to the cavity portion 19 prevents bubbles, droplets, tooth powders, or the like from sticking to the optical window provided in the head portion 113.

Portions of the device beyond the toothbrush base 6 and the video scope base 107 advance into the mouth to pick up images of the teeth and the gums while performing the brushing operation. When the toothbrush is placed so as to brush a particular tooth, the angle of visibility or the focal length or depth of the image pickup system or the illumination angle or intensity of the illumination means is adjusted so that a tip portion of the brush 1 is located in a peripheral portion or a corner of the picked-up image while the teeth to be brushed is located in a central portion thereof.

As described above, by imaging and illuminating the tooth through the cavity portion 19 of the head portion 2 of the toothbrush and adjusting the image pickup system and the illumination means so that the tip portion of the brush 1 is located in a peripheral portion or a corner of the picked-up image while the teeth to be brushed is located in a central portion thereof, the brushing operation can be preformed while actually viewing images to check whether a site observed with the video scope correspond to a site to be brushed.

Since the transparent film 26 stuck to the cavity portion 19 has its brush-1-side surface subjected to hydrophilic treatment, bubbles or droplets are likely to collapse thereon to prevent the image pickup from being hindered. Additionally, this hydrophilic treatment also has an anti-clouding effect to prevent a picked-up image from clouding at the start of operation. In this case, if the image clouds temporarily at the start of operation, the clouding is eliminated in a short time due to the small thickness and heat capacity of the transparent film 26.

Further, since the transparent film 26 is stuck to the side of the head portion opposite to that with the brush 1, it is distant from the tooth being brushed, and bubbles, droplets, tooth powders, or the like are thus unlikely to reach it.

Moreover, since the transparent film 26 has a very small thickness of 0.02 mm, its presence does not substantially affect image forming conditions. That is, when the toothbrush is installed and removed, image forming conditions such as the focal length need not be changed, thereby enabling the configuration to be simplified. This device is thus very practically effective.

In the above described Embodiment 8, the polyvinylidene chloride film has been shown as an example of the transparent film 26, but the transparent film 26 may comprise vinyl chloride, polyethylene, polypropylene, polyester, or the like. Additionally, the transparent film 26 need not necessarily be subjected to the hydrophilic treatment.

Further, in the above described Embodiment 8, the cavity portion 19 is blocked by the transparent film 26, but may be blocked by a transparent plate that may bury substantially all of the cavity portion 19. Thus, using the transparent plate instead of the transparent film 26 serves to prevent, bubbles, droplets, tooth powders, or the like from sticking to the optical window provided in the head portion 113.

Furthermore, in the above described embodiment, the transparent film 26 is provided on the side of the head portion opposite to that with the brush 1 transplanted thereon. The present invention, however, is not limited to this but the transparent film 26 may be provided on the same side as that with the brush 1 transplanted thereon.

In addition, in the above described Embodiment 8, the transparent film 26 is provided on the cavity portion 19 adjoining the video-scope-side outer surface of the head portion 2, but may be provided in any portion as long as it can block the cavity portion 19.

Furthermore, in the above described Embodiment 8, the cavity portion 19 need not necessarily be formed in the head portion 2 of the toothbrush. The cavity portion may be formed in the neck portion 3. In this case, the configuration of the video scope must be changed so that light from the object which has passed through the cavity portion formed in the neck portion 3 is incident on the optical window provided in the video scope head portion 113.

Embodiment 9

Figure 14:
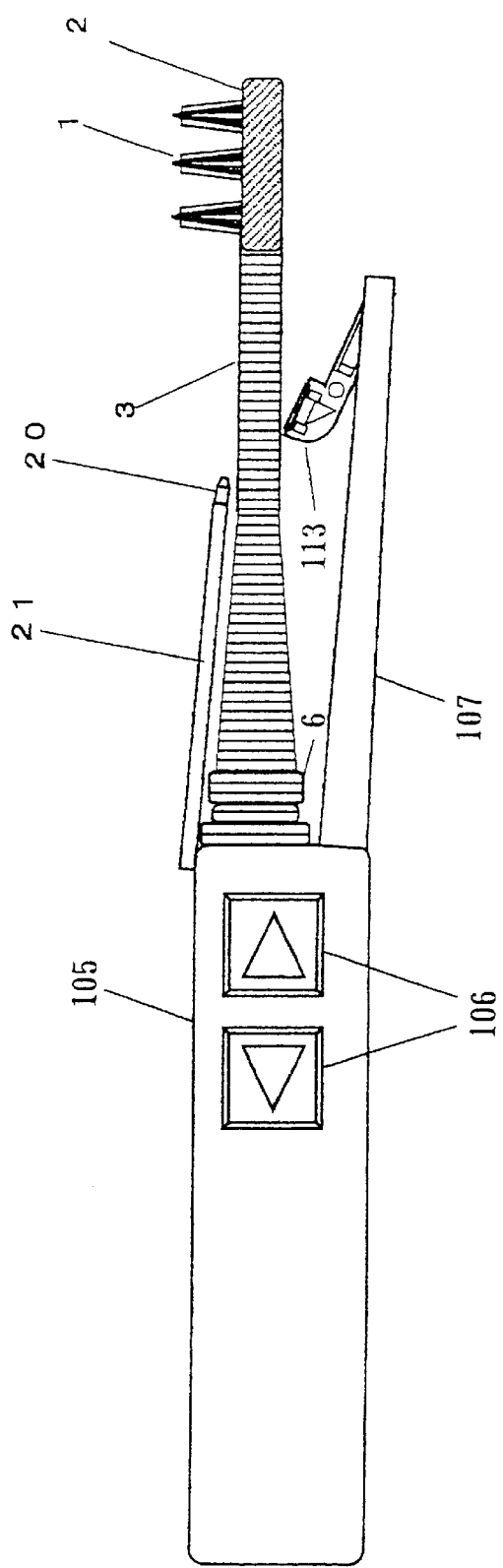
FIG. 14 is a side view of a main body of a tooth brushing device with a video scope according to Embodiment 9 of the present invention.

FIG. 14 is a side view of a main body of a tooth brushing device with a video scope according to Embodiment 9 of the present invention. Reference numerals 1 to 7 and 13 in FIG. 14 denote essentially the same components as reference numerals 1 to 7 and 13 in FIG. 9 except for the material of the neck portion 3, the shape of the video scope 107, and the structure and arrangement of the head portion 113.

Figure 17:
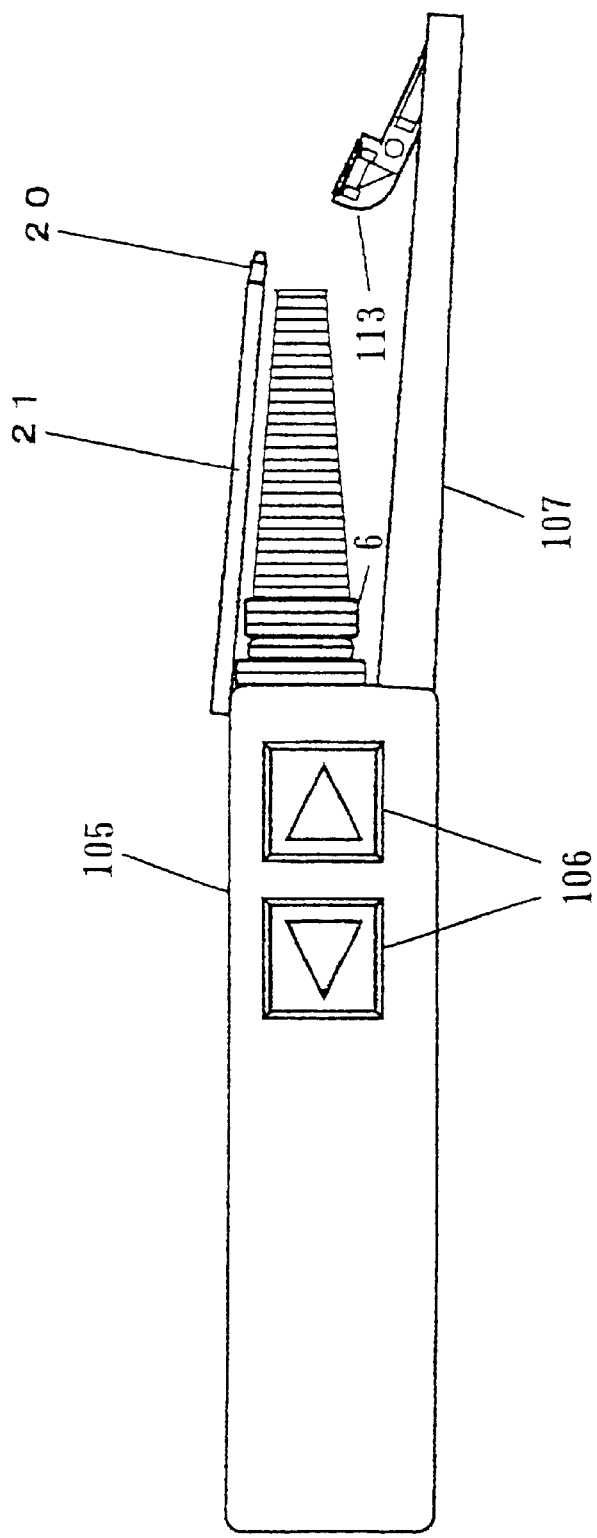
FIG. 17 is a view of the main body of the tooth brushing device with the video scope shown in FIG. 14 with a tooth brush section removed therefrom.
Figure 18:
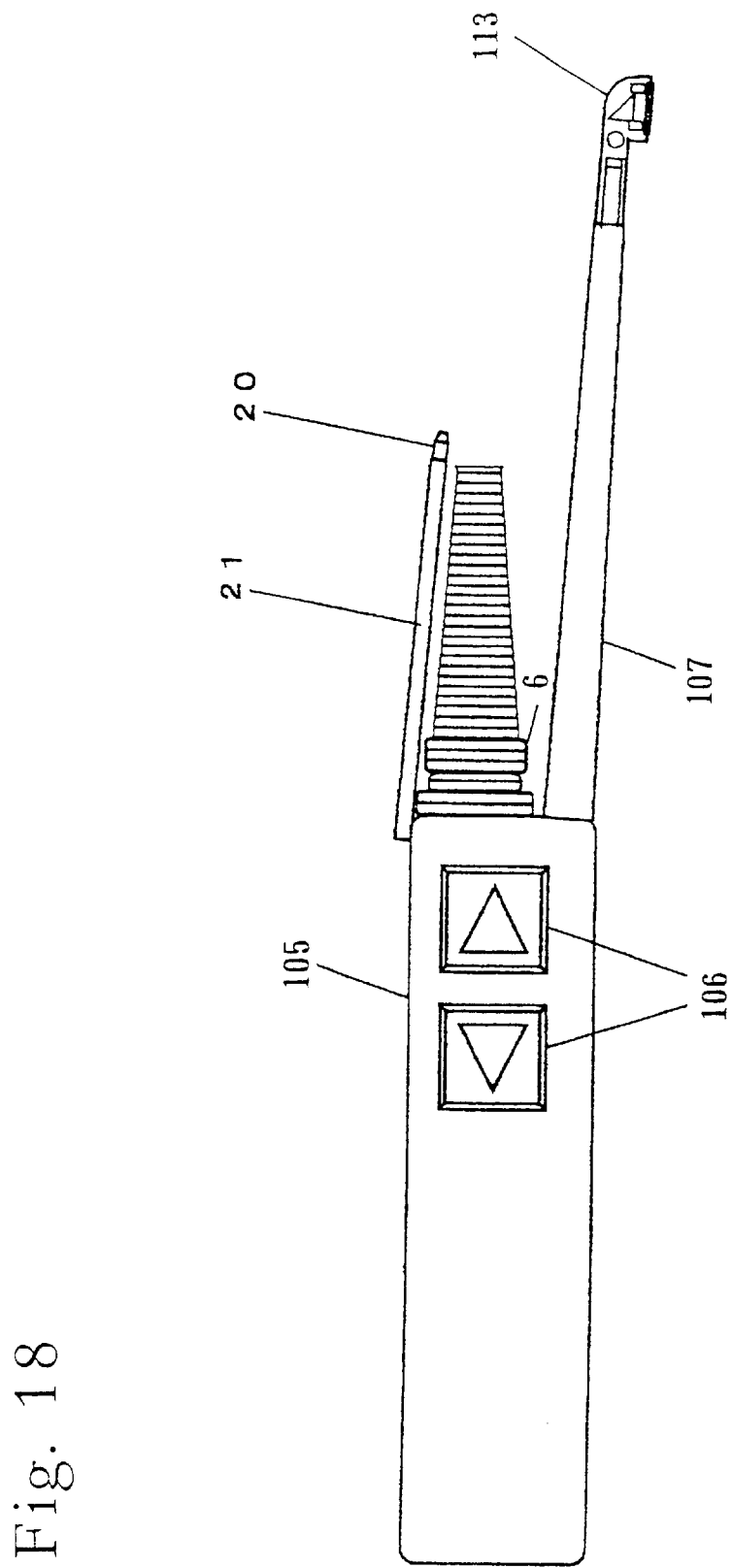
FIG. 18 is a view of the main body of the tooth brushing device with the video scope shown in FIG. 17 with a head portion rotationally moved.

In FIG. 14, the neck portion 3 comprises transparent polyethylene to constitute a transparent member. The video scope base 107 and the head portion 113 of the video scope are arranged as shown in FIG. 14 so that image pickup light is incident on the head portion 113 of the video scope through the transparent neck portion 3. Illumination light from the white LED housed in the head portion 113 also illuminates the object through the neck portion Portions of the device beyond the toothbrush base 6 and the video scope base 107 advance into the mouth to pick up images of the teeth and the gums while performing the brushing operation. When the toothbrush is placed so as to brush a particular tooth, the angle of visibility or the focal length or depth of the image pickup system or the illumination angle or intensity of the illumination means is adjusted so that the tip portion of the brush 1 is located in an end of the picked-up image while the teeth to be brushed is located in a central portion thereof. Then, when the toothbrush is removed as shown in FIGS. 17 and 18, that is, in order to enable images to be picked up without relying on the neck portion 3 comprising the transparent member, the image forming conditions such as the focal length can be changed by changing the stop diameter of the iris in the head portion 113 and the positions of the objective lens and the CCD. This is convenient in simply observing the inside of the mouth rather than performing the tooth brushing operation.

FIG. 18 shows that the head portion 113 is rotatably attached to the video scope base 107 and has been rotationally moved to the illustrated position after the toothbrush has been removed. This device is easier to operate than that shown in FIG. 17 because the distance from the root to the head portion of the handle section 105 is larger and because the head portion is located at the tip portion.

Additionally, in FIGS. 17 and 18, the toothbrush can be removed from the boundary between the neck portion 3 and the toothbrush base 6, the present invention is not limited to this but it may be removed from the boundary between the toothbrush base 6 and the handle section 105.

Further, in this embodiment, the head portion 113 extends in a fashion being bent from the tip portion of the video scope base 107 toward the handle section 105, the present invention is not limited to this but the tip portion of a video scope base shorter than the video scope base 107 shown in FIG. 14 may face the neck portion 3 and the video scope head portion may be attached straight to the tip portion in the direction of an extension thereof. In this case, the head portion receives light from the object which has passed through the neck portion 3 comprising the transparent member as described above.

The above described configuration shown in FIGS. 17 and 18 are applicable to the configuration in FIG. 5.

Furthermore, the neck portion 3 comprising transparent polyethylene has its side with the brush 1 transplanted thereon subjected to water-repellent treatment using a silane coupling agent having a straight alkyl chain represented by $CF_3(CF_2)_n(CH_2)2SiCl_3$ (where n is an integer equal to or larger than 0 or 1) This water-repellent treatment results in a film thickness of 10 nm or less, which allows visible light to be substantially completely transmitted through the film.

Reference numeral 20 denotes a nozzle that injects a gas such as air which has been delivered through a pipe 21, onto the neck portion 3. The injection of the gas is controlled by the switch 106.

During the tooth brushing operation, bubbles or droplets are likely to occur and these bubbles or droplets or tooth powders may stick to the neck portion 3 to hinder the image pickup. In this case, when the operator operates the switch 106, air is injected onto the neck portion 3 through the nozzle 20 to remove the extraneous matters such as the bubbles, droplets, and tooth powders therefrom. When a picked-up image or the like shows that all the extraneous matters have been removed and the operator then operates the control switch 106 to stop injecting air, a clear image of the target tooth or gum is picked up again. In this case, since the neck portion 3 has been subjected to the water-repellent treatment, the bubbles or droplets are easily removed by means of the injection of the gas such as air.

As described above, when the means for injecting the gas onto the transparent neck portion 3 is provided and controlled by the operator and if bubbles, droplets, tooth powders, or the like stick to the transparent neck portion 3 to hinder the image pickup while the operator is performing the tooth brushing operation while actually viewing an image to check whether the site observed by the video scope corresponds to the site to be brushed by the toothbrush, then these extraneous matters can be removed. This enables the checking with a stable image even during the tooth brushing operation. This device is thus very practically effective.

In addition, in the above described Embodiment 9, a blowing pump or the like built into the handle section 105 may be used to inject air, the injected liquid need not be supplied as in Embodiment 5, thereby eliminating the needs for cords. However, a nozzle for injecting the liquid such as water may be used instead of the nozzle 20 for injecting the gas. In short, the nozzle 20 provided as the injection means for injecting the gas or the nozzle provided as the injection means for injecting the liquid has only to remove the bubbles, droplets, tooth powders, or the like which have stuck or are to stick to the neck portion 3.

Furthermore, the video scope according to this embodiment has its image forming conditions switched between two phases depending on the presence of the toothbrush, that is, the shape of the video scope base 107 in FIG. 14 can be changed by rotationally moving the tip portion thereof beyond the bent portion thereof on the extension of the main body of the video scope base 107. Consequently, this video scope can also be easily used to simply observe the inside of the mouth and thus has a broad range of applications (see FIG. 18).

In the above described Embodiment 9, polyethylene has been shown as an example of the transparent member constituting the neck portion 3, but the transparent member constituting the neck portion 3 may be transparent methyl polyacrylate, polymethyl methacrylate, polycarbonate, or polypropylene.

Additionally, in the above described Embodiment 9, the water-repellent treatment using the silane coupling agent having the straight alkyl chain represented by $CF_3(CF_2)_n(CH_2)2SiCl_3$ (where n is an integer equal to or larger than 0 or 1) has been shown a an example of the water-repellent treatment. Dimethyl silicon-based organic polymer water repellent treatment agent, however, may be used instead as long as visible light can be transmitted through the resulting film.

Further, the nozzle 20 as the injection means in the above described Embodiment 9 may be arranged in the handle section 105 as shown in FIG. 14 or, for example, between the handle portion 105 and the neck portion 3 of the toothbrush. In short, the nozzle 20 as the injection means need not necessarily be arranged in the handle section 105.

Further, in the above described Embodiment 9, the control switch 106 provided in the handle section 105 has been described as the means for controlling the operation of the toothbrush and the injection of the gas, but a means for controlling only the operation of the toothbrush and a means for controlling the injection of the liquid or the gas may be separately provided.

This embodiment may further include the means for removing bubbles, droplets, tooth powders, or the like which have stuck or are to stick to the optical window of the head portion 113 of the video scope shown in FIG. 14, for example, the injection means for injecting the liquid such as water or the gas such as water, the wiping means for wiping extraneous matters off from the optical window, or the vibration means for vibrating the optical window as described in Embodiments 5 to 7. The injection means, the wiping means, or the vibration means may be controlled by the control switch 106 or a control means for controlling the injection means, the wiping means, or the vibration means may be provided in the handle section 105 separately from the control switch 106;

Embodiment 10

Figure 15:
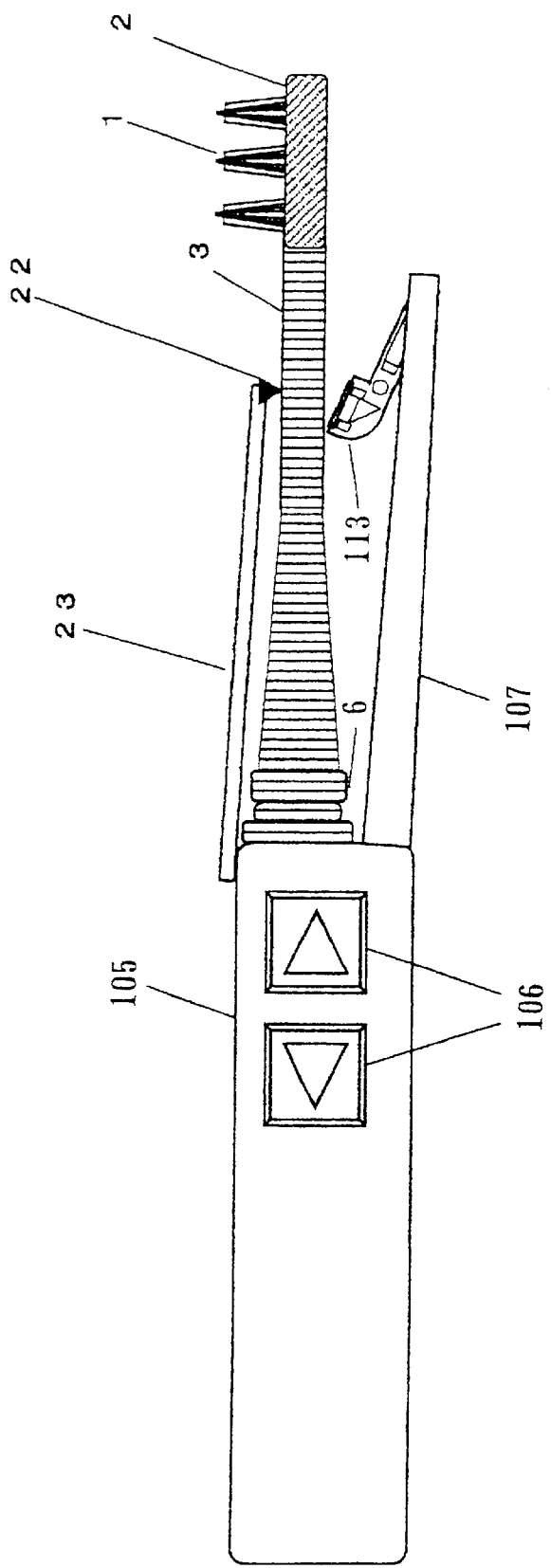
FIG. 15 is a side view of a main body of a tooth brushing device with a video scope according to Embodiment 10 of the present invention.
Figure 16:
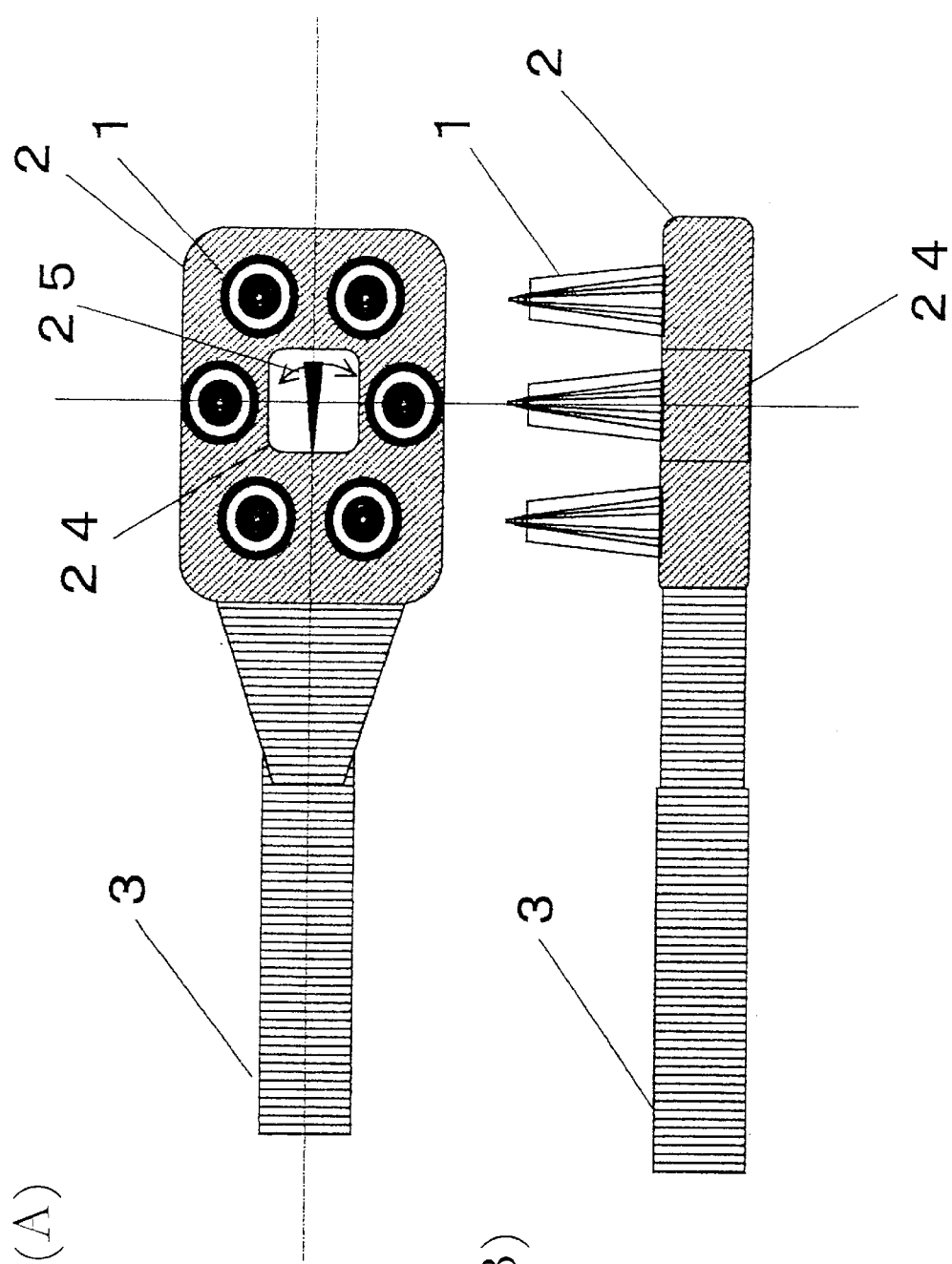
FIG. 16(A) is a top view showing the configuration of a main body of a tooth brushing device with a video scope according to Embodiment 11 of the present invention.
FIG. 16(B) is a side view of a tooth brush according to the embodiment shown in FIG. 16(A)

FIG. 15 is a side view of a main body of a tooth brushing device with a video scope according to Embodiment 10 of the present invention. Reference numerals 1 to 7 and 13 in FIG. 14 denote the same components as reference numerals 1 to 7 and 13 in FIG. 9 which function in the same manner as those in FIG. 9.

Reference numeral 22 denotes a rubber brush for removing bubbles, droplets, tooth powders, or the like from the brush-1-side of the neck portion 3, the brush 22 being coupled to the handle section 105 via a fixing base 23. When the neck portion 3 reciprocates for the tooth brushing operation, the brush 22 reciprocates over a surface of the neck portion 3 to remove the bubbles, droplets, tooth powders, or the like therefrom. In this case, the bubbles or droplets can be more easily removed by subjecting the neck portion 3 to water-repellent treatment.

As described above, when the means for wiping the neck portion 3 is provided and if bubbles, droplets, or tooth powders stick to the neck portion 3 to hinder the image pickup while the operator is performing the tooth brushing operation while actually viewing an image to check whether the site observed by the video scope corresponds to the site to be brushed by the tooth brush, then these extraneous matters can be removed. This enables the checking with a stable image even during the tooth brushing operation.

This embodiment is very practically effective because the wiping means, that is, the brush 22 can be fixed to the handle section 105 through the fixing base 23, so that the operation of the toothbrush and the operation of the brush 22 can be simultaneously controlled using the control switch 106, that is, the drive means for the electric toothbrush.

The neck portion 3 according to this embodiment may comprise polycarbonate or transparent methyl polyacrylate, polymethyl methacrylate, polyethylene, or polypropylene.

Additionally, the water-repellent treatment may use a silane coupling agent having a straight alkyl chain represented by $CF_3(CF_2)_n(CH_2)2SiCl_3$ (where n is an integer equal to or larger than 0 or 1) or may use dimethyl silicon-based organic polymer water repellent treatment agent as long as visible light can be transmitted through the resulting film.

Further, the operation of the brush 22 need not necessarily be linked with the operation of the toothbrush but a means for controlling the operation of the brush 22 separately from the operation of the toothbrush may be provided in the handle section 105.

Moreover, in the above described Embodiment 10, the brush 22 is made of rubber but its material is not limited to rubber. In short, the brush 22 may comprise any material as long as it can wipe extraneous matters off from the neck portion 3 without substantially damaging it.

This embodiment may further include the means for removing bubbles, droplets, tooth powders, or the like which have stuck or are to stick to the optical window of the head portion 113 of the video scope shown in FIG. 15, for example, the injection means for injecting the liquid such as water or the gas such as air, the wiping means for wiping extraneous matters off from the optical window, or the vibration means for vibrating the optical window as described in Embodiments 5 to 7. The injection means, the wiping means, or the vibration means may be controlled by the control switch 106 or a control means for controlling the injection means, the wiping means, or the vibration means may be provided in the handle section 105 separately from the control switch 106.

In addition, in the above described Embodiment 10, the brush 22 as the wiping means may be provided in the handling section 105 via the fixing base 23 as shown in FIG. 10 or for example, in the video scope base 107. In short, the brush 22 as the injection means need not necessarily be arranged in the handle section 105 via the fixing base 23.

Furthermore, in Embodiments 9 and 10, substances that have stuck or are to stick to the transparent neck portion 3 are removed by the injection means for injecting air or the liquid or by the wiping means, but may be removed by the vibration means for vibrating the neck portion 3 as described in Embodiment 7. A vibration control function for the vibration means may be provided for the control switch 106 or a control means for controlling only the vibration means may be arranged in the handle section 105 separately from the control switch 106.

Embodiment 11

FIGS. 16(A) and 16(B) show a toothbrush according to Embodiment 11 having a transparent portion in a head portion with a brush transplanted thereon. In FIGS. 16(A) and 16(B), reference numeral 1 denotes the brush, reference numeral 2 denotes the head portion with the brush 1 transplanted thereon, reference numeral 3 denotes a neck portion for supporting the head portion 2. Reference numeral 24 denotes the transparent portion arranged in the head portion 2, the transparent portion comprising transparent methyl polymethacrylate.

Image pickup light is incident on the video scope head portion 113 through the transparent portion 24. Illumination light from the white LED housed in the head portion 113 also illuminates the object through the cavity portion 24. Although FIGS. 16(A) and 16(B) do not show a video scope, a toothbrush and a video scope are attached to a common handle section as shown in FIG. 13.

The head portion 2 and the video scope head portion 113 advance into the mouth to pick up images of the teeth and the gums while performing the brushing operation. When the toothbrush is placed so as to brush a particular tooth, the angle of visibility or the focal length or depth of the image pickup system or the illumination angle or intensity of the illumination means is adjusted so that the tip portion of the brush 1 is located in a peripheral portion or a corner of the picked-up image while the teeth to be brushed is located in a central portion thereof. Then, when the tooth brush is removed, that is, in order to enable images to be picked up without using the transparent portion 24, the image forming conditions such as the focal length can be changed by changing the stop diameter of the iris in the head portion and the positions of the objective lens and the CCD. This is convenient in observing the inside of the mouth while not performing the tooth brushing operation. The image forming conditions such as the focal length may be manually or automatically switched.

Reference numeral 25 denotes a rubber brush for removing bubbles, droplets, tooth powders, or the like from the brush-1-side surface of the transparent portion 24, the brush having its operation controlled by the switch 106.

During the tooth brushing operation, bubbles or droplets are likely to occur and these bubbles or droplets or tooth powders may stick to the brush-1-side surface of the transparent portion 24 to hinder the image pickup. In this case, the operator operates the switch 106 to operate the brush 25 to remove the extraneous matters such as the bubbles, droplets, and tooth powders therefrom. When a picked-up image or the like shows that all the extraneous matters have been removed, the operator may operate the control switch 106 to stop the operation of the brush 25.

As described above, when the wiping means is provided on the brush-1-side surface of the transparent portion 24 in the head portion 2 and is controlled by the operator and if bubbles, droplets, tooth powders, or the like stick to the transparent neck portion to hinder the image pickup while the operator is performing the tooth brushing operation while actually viewing an image to check whether the site observed by the video scope corresponds to the site to be brushed by the tooth brush, then these extraneous matters can be removed. This enables the checking with a stable image even during the tooth brushing operation. This device is thus very practically effective.

The transparent portion 24 according to this embodiment may be subjected to hydrophilic treatment using methyl polymethacrylate. Alternatively, the transparent portion 24 may comprise polyvinylidene chloride, vinyl chloride, polyethylene, polypropylene, polyester, or another transparent material.

Further, the operation of the brush 25 need not necessarily be linked with the operation of the toothbrush but a means for controlling the operation of the brush 25 separately from the operation of the toothbrush may be provided in the handle section.

Moreover, in the above described Embodiment 11, the brush 25 is made of rubber but its material is not limited to rubber. In short, the brush 25 may comprise any material as long as it can wipe extraneous matters off from the transparent portion 24 without substantially damaging it.

The above described Embodiments 5 to 11 enables the user to observe or check the inside of the mouth while simultaneously performing a maintenance operation such as tooth brushing. This device is thus very practically effective.

All or part of each of the optical window, the transparent neck portion 3, the transparent portion 24, and the transparent film 26 in the above described Embodiments 5 to 11 may have its surface subjected to water-repellent treatment. The water-repellent treatment may use the water-repellent treatment agent described in Embodiments 10 or 11.

Additionally, in the above described Embodiments 5 to 11, the optical window is arranged in such a manner that its normal extends in the same direction as the brush 1 as shown in, for example, FIG. 9 or 13, but the position and direction of the optical window are not limited to those shown in FIG. 9 or 13. For example, the optical window may be arranged so that its normal is substantially perpendicular or at 60° to the direction of the brush 1. Furthermore, the optical window may be arranged in a lateral direction so as to lie at the side of a surface of the head portion 2 of the toothbrush other than that with the brush 1 transplanted thereon or so that its normal is substantially perpendicular or at 60° to the direction of the brush 1.

In addition, in the above described Embodiments 5 to 11, the handle section 105 is used as an example of the first handle section of the video scope and the second handle section of the toothbrush in the tooth brushing device with the video scope according to the present invention.

Further, the tooth brushing device with the video scope in each of the above described Embodiments 5 to 11 need not necessarily be used, by the operator only to brush his or her teeth. It may be used while the operator is not brushing his or her teeth.

Moreover, images picked up by the tooth brushing device with the video scope in each of the above described Embodiments 5 to 11 are transmitted to and displayed on a predetermined display.

Furthermore, the tooth brushing device with the video scope in each of the above described Embodiments 5 to 1 is not limited to an electric toothbrush.

In the above described embodiments, extraneous matters are removed from the surface of either the transmission window of the video scope or the transparent portion of the toothbrush, which transmits light from the object, or such sticking is prevented. The present invention, however, is not limited to this but the above described removal means or sticking preventing mechanism may be applied to both the transmission section and the transparent portion.

Additionally, in the above described embodiments, the vibration means according to the present invention is applied to the transmission window of the video scope. The present invention, however, is not limited to this but the vibration means may be applied to the transparent portion of the toothbrush or may be simultaneously, applied to both of them.

Figure 19:
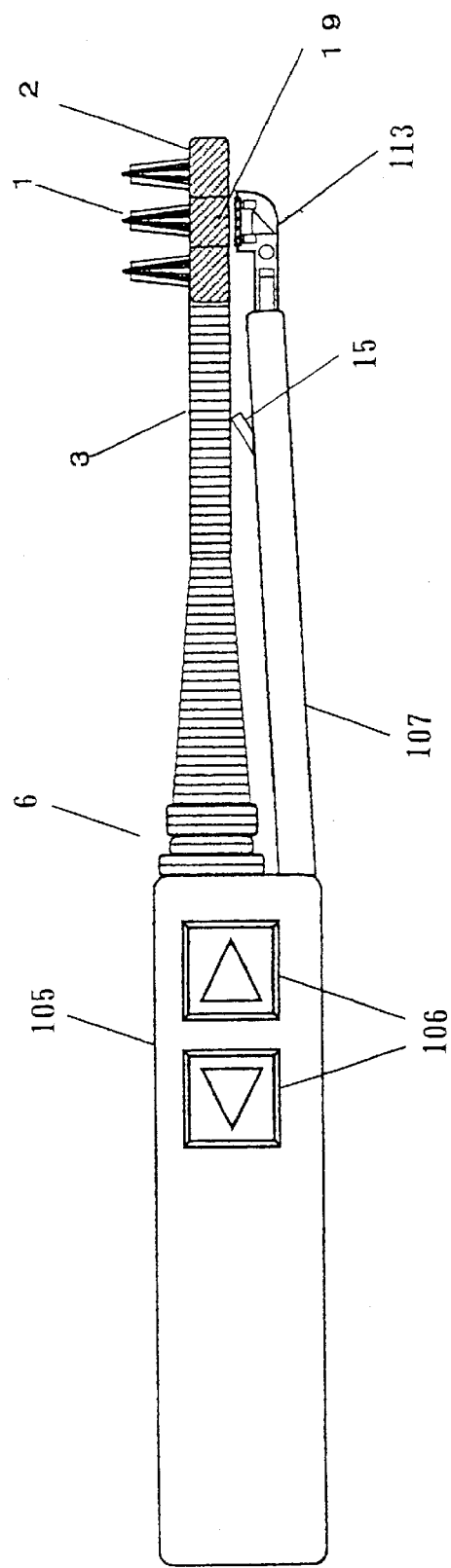
FIG. 19 is a side view showing that a light guide shown in FIG. 6 is applied to the main body of the tooth brushing device with the video scope shown in FIG. 13.

Further, in the above described embodiments, the head portion has the built-in illumination means if extraneous matters are removed from the surface of either the transmission window of the video scope or the transparent portion of the toothbrush, which transmits light from the object, or such sticking is prevented. The present invention, however, is not limited to this but the illumination means may be arranged at a position separate from the head portion (see FIG. 19). FIG. 19 shows an example where the light guide 15 shown in FIG. 6 is applied to the main body of the tooth brushing device with the video scope shown in FIG. 13.

As is apparent from the above description, the present invention allows the user to view the inside of the mouth through the video scope while more reliably brushing the tooth being viewed, thereby enabling an efficient and reliable tooth brushing operation without missing teeth to be brushed.

Additionally, the present invention can provide a tooth brushing device with a video scope that obtains clear images even during the tooth brushing operation by removing image pickup obstacles such as bubbles, droplets, or tooth powders if such obstacles have stuck or are to stick to the optical window (transmission window) of the image pickup means which faces the object or the transparent portion of the video scope.

Further, the present invention can provide a tooth brushing device with a video scope that obtains clear images even during the tooth brushing operation by preventing image pickup obstacles from sticking to the optical window (transmission window).

What is claimed is:

1. A tooth brushing device comprising:
   a video scope having image forming means of forming an image from light from an object, and an image pickup element for converting the light formed into the image by means of said image forming means, into an electric signal;
   a toothbrush having a brush section; and
   a display section for displaying the image picked up by said video scope, wherein:
      said video scope and said toothbrush each being supported by a common handle such that they may be used at the same time by an operator, and
      said image forming means being arranged such that a tooth is imaged by said video scope when the operator brushes the tooth.

2. The tooth brushing device of claim 1, wherein said image forming means is partly arranged on a rear side of a part of said brush section having a brush transplanted thereon.

3. The tooth brushing device of claim 1 or 2, comprising illumination means of illuminating the object.

4. The tooth brushing device of any of claims 1 or 2, wherein said toothbrush has a predetermined optical cavity portion such that light from said object is incident on said image forming means through said optical cavity portion.

5. The tooth brushing device of claim 4, wherein said optical cavity portion is arranged in said brush section.

6. The tooth brushing device of claim 4, wherein said optical cavity portion is formed in an intermediate portion between said brush section of said tooth brush and said handle.

7. The tooth brushing device of claim 4, wherein illumination light illuminates said object through said optical cavity portion.

8. The tooth brushing device of claim 7, wherein said optical cavity portion is formed in said brush section and in an intermediate portion between said brush section and the handle,
   light from said object is incident on said image forming means through said optical cavity portion in one of said brush section and said intermediate portion, and
   the illumination light illuminates said object through the other of said brush section and said intermediate portion.

9. The tooth brushing device of claim 4, wherein said optical cavity portion has a transparent member through which light is transmitted.

10. The tooth brushing device of claim 9, wherein said transparent member has at least its surface facing said object subjected to hydrophilic treatment or has an attachment removing means on said surface for removing extraneous matters therefrom.

11. The tooth brushing device of claim 1, wherein said video scope picks up an image in a manner such that a tip of said brush section is located at an end of the picked-up image.

12. The tooth brushing device of claim 1, wherein said toothbrush is an electric toothbrush.

13. The tooth brushing device of claim 12, wherein at least said brush section of said electric toothbrush is movable independently of said handle.

14. The tooth brushing device of claim 1, wherein said picked-up image is transmitted to said display section by means of a predetermined electric wave.

15. The tooth brushing device of claim 12, wherein said display section is arranged in a charger for charging said electric toothbrush or in a holder for holding said handle while the device is not in use.

16. The tooth brushing device of claim 1, wherein said video scope has a transmission window through which said light between said image forming means and said object is transmitted, and the device comprises removal means of removing extraneous matters from said transmission window.

17. A tooth brushing device comprising:

a video scope having a transmission window through which light from an object is transmitted, image forming means of forming an image from the light from said object which has been transmitted through said transmission window, and an image pickup element for converting the light formed into the image by means of said image forming means, into an electric signal;

a toothbrush having a brush section; and a removal means of removing extraneous matters from said transmission window, wherein:

said video scope and said toothbrush each being supported by a common handle such that they may be used at the same time by an operator.

18. The tooth brushing device of claim 17, wherein said removal means is injection means of injecting a liquid and/or a gas.

19. The tooth brushing device of claim 17, wherein said removal means is wiping means of wiping extraneous matters off from said transmission window.

20. The tooth brushing device of claim 17, wherein said removal means is vibration means of vibrating said transmission window.

21. The tooth brushing device of claim 17, comprising control means of controlling operations of said removal means, said control means being arranged in said handle.

22. The tooth brushing device of claim 17, wherein said toothbrush is an electric toothbrush and comprises:

driver means of driving the brush section of said electric toothbrush, said drive means being arranged in said handle, said drive means being also capable of controlling operations of said removal means.

23. The tooth brushing device of claim 17, wherein said transmission window is subjected to water-repellent or hydrophilic treatment that allows visible light to be transmitted therethrough.

24. A tooth brushing device comprising:

a video scope having a transmission window through which light from an object is transmitted, image forming means of forming an image from the light from said object which has been transmitted through said transmission window, and an image pickup element for converting the light formed into the image by means of said image forming means into an electric signal; and a toothbrush having a transparent portion through which the light from said object is transmitted, and a brush section, wherein:

said transparent portion has at least its surface facing said object subjected to hydrophilic treatment or has a first removal means on said surface for removing extraneous matters therefrom, said video scope and said toothbrush each being supported by a common handle such that they may be used at the same time by an operator, said transparent portion is arranged between said brush section of said toothbrush and said handle or in said brush section of said toothbrush, and said transmission window is arranged such that the light from said object which has been transmitted through said transparent portion is transmitted therethrough.

25. The tooth brushing device of claim 17 or 24, comprising illumination means of illuminating the object.

26. The tooth brushing device of claim 24, wherein image pickup conditions for said video scope can be switched so as to pick up a clear image of said object whether said image forming means forms an image from the light from said object which has or has not been transmitted through said transparent portion.

27. The tooth brushing device of claim 24 or 26, comprising second removal means of removing extraneous matters from said transmission window.

28. The tooth brushing device of claim 27, wherein said first removal means and/or said second removal means are/is injection means of injecting a liquid and/or a gas.

29. The tooth brushing device of claim 27, wherein said first removal means and/or said second removal means are/is wiping means of wiping extraneous matters off from said transmission window and/or said transparent portion.

30. The tooth brushing device of claim 27, wherein said first removal means and/or said second removal means are/is vibration means of vibrating said transmission window and/or transparent portion.

31. The tooth brushing device of claim 27, comprising control means of controlling operations of said first removal means and/or said second removal means, said control means being arranged in said handle.

32. The tooth brushing device of claim 27, wherein said toothbrush is an electric toothbrush and comprises:

drive means of driving the brush section of said electric toothbrush, said drive means being arranged in said handle, said drive means being also capable of controlling operations of said first removal means and/or said second removal means.

33. The tooth brushing device of claim 24, wherein the light is applied to said object through said transparent portion.

34. The tooth brushing device of claim 24, wherein all or part of said transmission window, and said transparent portion is subjected to water-repellent or hydrophilic treatment that allows visible light to be transmitted therethrough.

35. A tooth brushing device comprising:

a video scope having a transmission window through which light from an object is transmitted, image forming means of forming an image from the light from said object which has been transmitted through said transmission window, and an image pickup element for converting the light formed into the image by means of said image forming means into an electric signal; and a toothbrush having a brush section, and a through-hole, wherein:

said video scope and said toothbrush each being supported by a common handle such that they may be used at the same time by an operator, said through-hole is covered by a transparent member, and said transmission window providing for transmission of the light transmitted through said transparent member while said image forming means forms the image from the light from said object which has been transmitted through said transparent member and said transmission window.

36. The tooth brushing device of claim 35, wherein said transparent member is a transparent film or plate.

37. The tooth brushing device of claim 36, wherein said through-hole is formed in said brush section, and said transparent film is arranged in a portion adjoining an outer surface of said brush section of said video scope.

38. The tooth brushing device of claim 35, wherein all or part of said transmission window and said transparent member is subjected to water-repellent or hydrophilic treatment that allows visible light to be transmitted therethrough.

39. The tooth brushing device of claim 23, 34, or 38, wherein said water-repellent treatment uses a dimethyl silicon-based organic polymer water-repellent treatment agent or a silane coupling agent having a straight alkyl chain.

* * * * *